(12) United States Patent
Lee et al.

(10) Patent No.: US 12,390,505 B2
(45) Date of Patent: Aug. 19, 2025

(54) COMPOSITION FOR PREVENTING OR TREATING OBESITY OR DIABETES, COMPRISING ACANTHOPANAX SENTICOSUS EXTRACT AND GARCINIA CAMBOGIA EXTRACT OR COMPOUND ISOLATED THEREFROM

(71) Applicant: KOREA RESEARCH INSTITUTE OF BIOSCIENCE AND BIOTECHNOLOGY, Daejeon (KR)

(72) Inventors: Su Ui Lee, Daejeon (KR); Hyung Won Ryu, Daejeon (KR); Mun Ock Kim, Daejeon (KR); Sei Ryang Oh, Daejeon (KR); Doo Young Kim, Daejeon (KR); Hyun Jae Jang, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 402 days.

(21) Appl. No.: 18/024,604

(22) PCT Filed: Aug. 18, 2021

(86) PCT No.: PCT/KR2021/010925
§ 371 (c)(1),
(2) Date: Mar. 3, 2023

(87) PCT Pub. No.: WO2022/050601
PCT Pub. Date: Mar. 10, 2022

(65) Prior Publication Data
US 2023/0364170 A1    Nov. 16, 2023

(30) Foreign Application Priority Data

Sep. 3, 2020 (KR) .................. 10-2020-0112341
Jun. 10, 2021 (KR) .................. 10-2021-0075749

(51) Int. Cl.
*A61K 36/258* (2006.01)
*A61K 31/194* (2006.01)
(Continued)

(52) U.S. Cl.
CPC .......... *A61K 36/258* (2013.01); *A61K 31/194* (2013.01); *A61K 31/585* (2013.01);
(Continued)

(58) Field of Classification Search
CPC ................ A61K 36/258; A61K 31/194; A61K 31/585; A61K 36/38; A61P 3/04; A61P 3/08
See application file for complete search history.

(56) References Cited

FOREIGN PATENT DOCUMENTS

| | | |
|---|---|---|
| CN | 101253903 A | 9/2008 |
| KR | 10-2001-0103065 A | 11/2001 |

(Continued)

OTHER PUBLICATIONS

Yu Hwa Park et al., "Effects of Ethanol Extract from Leaves of Eleutherococcus senticosu on Hyperlipidemia in Rats", J Korean Soc Food Sci Nutr, 2012, pp. 333-338, vol. 41, No. 3.

(Continued)

*Primary Examiner* — Trevor Love
(74) *Attorney, Agent, or Firm* — Sughrue Mion, PLLC

(57) ABSTRACT

The present invention relates to a pharmaceutical composition for preventing or treating obesity or diabetes, and to a food composition and feed composition for preventing or alleviating obesity or diabetes, comprising as an active ingredient, an *Acanthopanax* extract, a *Garcinia cambogia* extract, or compounds isolated therefrom. The composition has synergistic antidiabetic and antiobesity activity compared to that of using only an *Acanthopanax* extract, a *Garcinia cambogia* extract, or compounds isolated therefrom. Therefore, it is possible to reduce the possibility of any side effects that may be caused by an overdose of or long-term administration of the *Garcinia cambogia* extract and a substance isolated therefrom, and thus the composition can be very effectively utilized in the development of a therapeutic agent for diabetes or obesity.

10 Claims, 5 Drawing Sheets

Specification includes a Sequence Listing.

(51) Int. Cl.
  *A61K 31/585* (2006.01)
  *A61K 36/38* (2006.01)
  *A61P 3/04* (2006.01)
  *A61P 3/08* (2006.01)

(52) U.S. Cl.
  CPC ............... *A61K 36/38* (2013.01); *A61P 3/04* (2018.01); *A61P 3/08* (2018.01)

(56) References Cited

FOREIGN PATENT DOCUMENTS

| KR | 10-0711056 B1 | 4/2007 |
| KR | 10-2015-0055876 A | 5/2015 |
| KR | 10-1956759 B1 | 3/2019 |

OTHER PUBLICATIONS

Neeru Vasudeva et al., "Natural Products: A safest Approach for Obesity", Chinese Journal of Integrative Medicine, Jun. 2012, pp. 473-480, vol. 18, No. 6.
Ilze Vermaak et al., "Natural products in anti-obesity therapy", Natural Product Reports, 2011, pp. 1493-1533, vol. 28.
International Search Report of PCT/KR2021/010925 dated Nov. 30, 2021 [PCT/ISA/210].
Written Opinion of PCT/KR2021/010925 dated Nov. 30, 2021 [PCT/ISA/237].
Hyun Young Kim, et al., "Protective Effects of 3,4-seco-lupane Type Triterpenes from *Acanthopanax senticosus* against Advanced Glycation Endproducts", Hort. Environ. Biotechnol, 2012, vol. 53, No. 3, pp. 242-246 (5 pages total).
Guanxing Liu, et al., "Effect and Mechanism of Garcinia cambogia Extract on Lipid Metabolism in Male Rats", Food Science, 2015, vol. 36, No. 9, pp. 202-208 (7 pages total).

COMPOSITION FOR PREVENTING OR TREATING OBESITY OR DIABETES, COMPRISING ACANTHOPANAX SENTICOSUS EXTRACT AND GARCINIA CAMBOGIA EXTRACT OR COMPOUND ISOLATED THEREFROM

CROSS REFERENCE TO RELATED APPLICATIONS

This application is a National Stage of International Application No. PCT/KR2021/010925 filed Aug. 18, 2021, claiming priority based on Korean Patent Application No. 10-2020-0112341 filed Sep. 3, 2020 and Korean Patent Application No. 10-2021-0075749 filed Jun. 10, 2021, the entire disclosures of which are incorporated herein by reference.

INCORPORATION BY REFERENCE OF SEQUENCE LISTING

The content of the electronically submitted sequence listing, file name: Q285704_sequence listing as filed.txt; size: 3,525 bytes; and date of creation: Mar. 3, 2023, filed herewith, is incorporated herein by reference in its entirety.

TECHNICAL FIELD

The present invention relates to a pharmaceutical composition for preventing or treating obesity or diabetes, and to a food composition and feed composition for preventing or alleviating obesity or diabetes, comprising as an active ingredient, an *Acanthopanax* extract, a *Garcinia cambogia* extract, or compounds isolated therefrom.

BACKGROUND ART

Changes in lifestyle and economic growth have changed people's eating habits, which has led to an increase in the overweight or obese population. About 30-40% of modern people are known to be obese, and it is predicted that the world's obese population will reach 1 billion by 2025.

As a method for improving obesity, there are various methods such as improvement of eating habits, intake of calorie-restricted foods, exercise therapy, and intake of drugs that inhibit fat absorption. However, the use of calorie-restricted foods increases the user's desire for food, while having side effects such as the occurrence of diseases due to deficiency/excess of nutrients.

In addition, taking a drug that inhibits fat absorption is known to cause side effects such as diarrhea, gastrointestinal side effects, and kidney disease.

Moreover, obesity is also a cause of adult diseases such as diabetes and high blood pressure. Diabetes is known as a metabolic disease characterized by hyperglycemia caused by secretion or dysfunction of insulin necessary for blood sugar control in the body. Diabetes causes macrovascular complications such as microvascular complications, arteriosclerosis, cardiovascular disease, and cerebrovascular disease in the retina, kidney, and nerves, and increases mortality due to these complications.

Currently used diabetes treatment methods include diet therapy, treatment methods using oral hypoglycemic agents such as metformin, sulfonylurea, alpha-glucosidase inhibitors, and thiazolidinedione and insulin, exercise therapy, and the like. However, diet therapy is difficult for patients to implement in daily life due to its complexity. In addition, it is known that ketoacidosis occurs when a diabetic patient exercises under a low insulin concentration, and hypoglycemia is induced when a diabetic patient exercises under an excessive insulin concentration. Furthermore, treatment using an oral hypoglycemic agent and insulin has a weak effect on lowering blood sugar in diabetic patients with beta cell dysfunction.

Therefore, as a new treatment for obesity or diabetes, there is a need to develop an effective treatment that has no side effects, especially using natural substances.

PRIOR ARTS

Patent Document (Patent Document 1) Korean Patent Application No. 10-1956759

DISCLOSURE

Technical Problem

Accordingly, the present inventors studied to develop a treatment for obesity and diabetes using natural substances, the present invention was completed by confirming that a composition obtained by mixing an *Acanthopanax* extract, a *Garcinia cambogia* extract, or a compound isolated therefrom in a predetermined ratio has excellent antidiabetic and antiobesity effects.

Technical Solution

One aspect of the present invention provides a pharmaceutical composition for preventing or treating diabetes or obesity, comprising *Acanthopanax* extract and *Garcinia cambogia* extract or a compound isolated therefrom as an active ingredient.

In addition, it provides a pharmaceutical composition for preventing or treating diabetes or obesity, consisting of *Acanthopanax* extract and *Garcinia cambogia* extract or a compound isolated therefrom.

In addition, it provides a pharmaceutical composition for preventing or treating diabetes or obesity, essentially consisting of *Acanthopanax* extract and *Garcinia cambogia* extract or a compound isolated therefrom.

Another aspect of the present invention provides a food composition for preventing or ameliorating diabetes or obesity, comprising *Acanthopanax* extract and *Garcinia cambogia* extract or a compound isolated therefrom as an active ingredient.

In addition, it provides a food composition for preventing or ameliorating diabetes or obesity, consisting of *Acanthopanax* extract and *Garcinia cambogia* extract or a compound isolated therefrom.

In addition, it a food composition for preventing or ameliorating diabetes or obesity, essentially consisting of *Acanthopanax* extract and *Garcinia cambogia* extract or a compound isolated therefrom.

Another aspect of the present invention provides a feed composition for preventing or ameliorating diabetes or obesity, comprising *Acanthopanax* extract and *Garcinia cambogia* extract or a compound isolated therefrom as an active ingredient.

In addition, it provides a feed composition for preventing or ameliorating diabetes or obesity, consisting of *Acanthopanax* extract and *Garcinia cambogia* extract or a compound isolated therefrom.

In addition, it a feed composition for preventing or ameliorating diabetes or obesity, essentially consisting of *Acanthopanax* extract and *Garcinia cambogia* extract or a compound isolated therefrom.

Another aspect of the present invention provides the use of an *Acanthopanax* extract and a *Garcinia cambogia* extract or a compound isolated therefrom for preparing an agent for the treating of diabetes or obesity.

A method of treating diabetes or obesity comprising administering an effective amount of a composition containing an *Acanthopanax* extract and a *Garcinia cambogia* extract to a subject in need thereof.

Advantageous Effects

According to the present invention, the composition comprising the extract of *Acanthopanax* and the extract of *Garcinia cambogia*, or a specific combination of compounds isolated therefrom effectively inhibits proliferation of fat cells, production of neutral fat and synthesis of body fat, and increases glucose absorption in muscle cells. In addition, the composition has synergistic anti-diabetic and anti-obesity activity compared to the case of using the extract of *Acanthopanax* extract and the extract of *Garcinia cambogia*, or a compound isolated therefrom alone. Therefore, it is possible to reduce the possibility of any side effects that may be caused by overdose or long-term administration of the *Garcinia cambogia* extract and the substances isolated therefrom, so that it can be very useful for the development of diabetes or obesity treatment.

MODES FOR THE INVENTION

Figure 1:
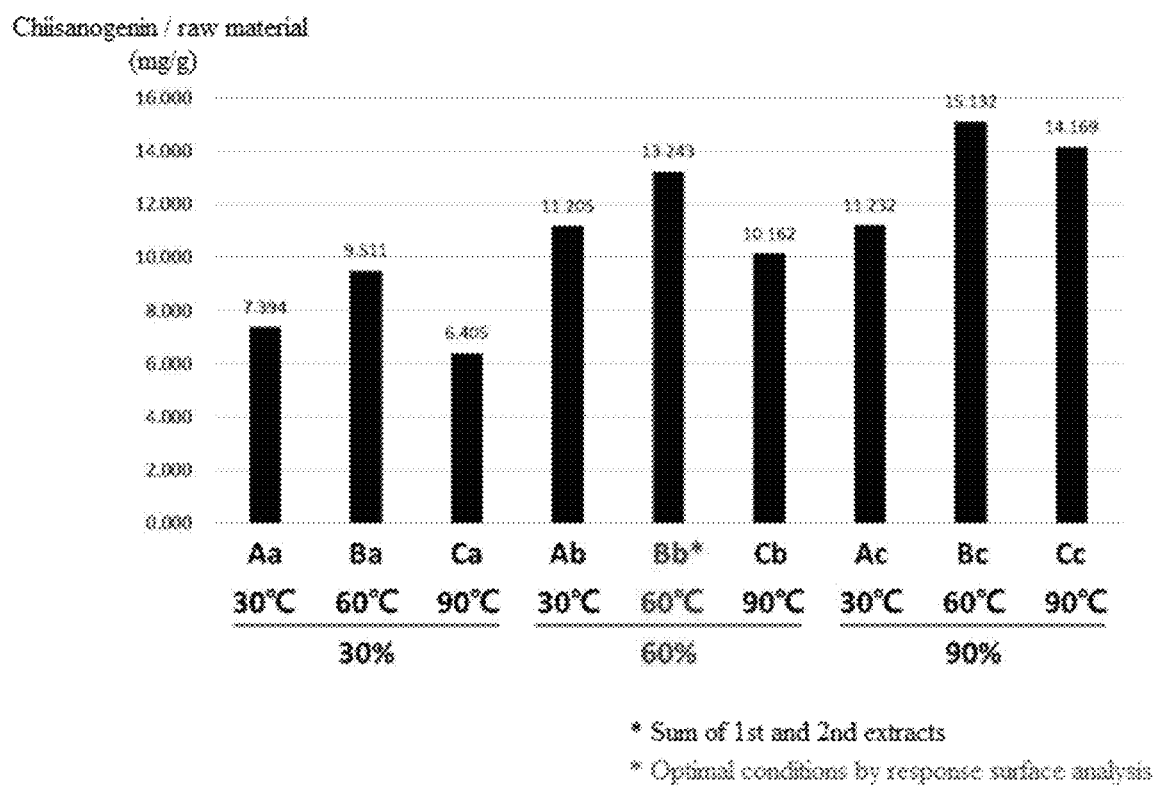
FIG. 1 is a graph showing the chiisanogenin content of the extract of *Acanthopanax* according to the concentration and temperature conditions of the ethanol solvent.
Figure 2:
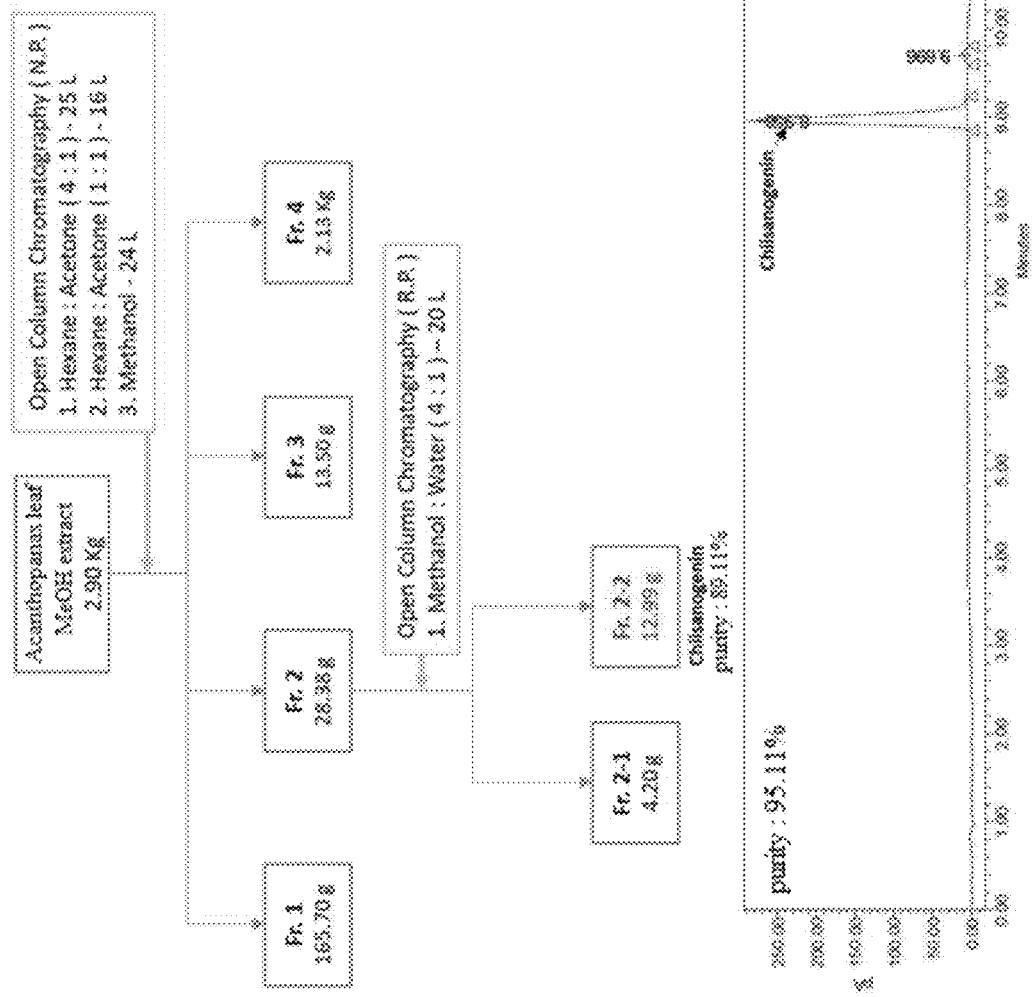
FIG. 2 is a schematic diagram of a method for separating chiisanogenin from the extract of *Acanthopanax*.
Figure 3:
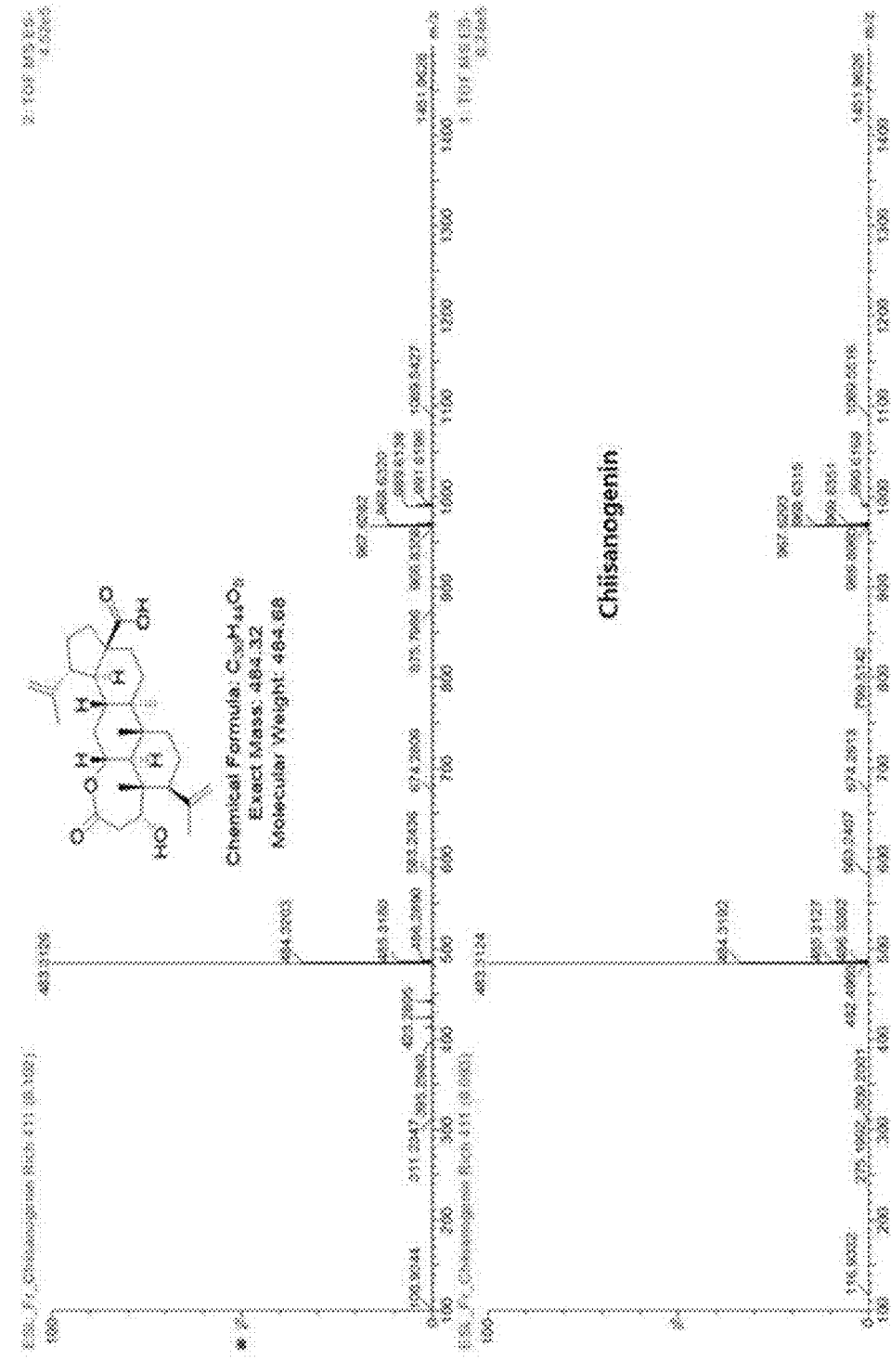
FIG. 3 shows the analysis results for the marker component separated from the extract of *Acanthopanax*.

Hereinafter, the present invention will be described in detail.

One aspect of the present invention provides a pharmaceutical composition for preventing or treating diabetes or obesity, comprising a first component of *Acanthopanax* extract, chiisanogenin, or chiisanogenin derivative, and a second component of *Garcinia cambogia* extract or hydroxy citric acid (HCA).

As used herein, the term "extract" refers to a product such as a liquid component obtained by immersing a desired material in various solvents and then extracting the material at room temperature, low temperature, or high temperature for a certain period of time, solid content obtained by removing the solvent from the liquid component. In addition, it can be comprehensively interpreted as including all dilutions of the results, concentrates thereof, dried products obtained by drying them, fractions, or crude products and purified products thereof.

A method for extracting *Acanthopanax* extract or *Garcinia* extract is a method commonly known in the art, and for example, a method using an extraction device such as solvent extraction, supercritical extraction, subcritical extraction, high temperature extraction, high pressure extraction or ultrasonic extraction or a method using an adsorption resin may be used.

Non-limiting examples of the extraction solvent include water; hydrocarbon solvents such as lower alcohols having 1 to 4 carbon atoms such as methanol, ethanol, propyl alcohol and butyl alcohol; polyhydric alcohols such as glycerin, butylene glycol, and propylene glycol; and methyl acetate, ethyl acetate, acetone, benzene, hexane, diethyl ether, dichloromethane or mixtures thereof may be used. In addition, the method for obtaining the extract is not particularly limited thereto as long as the extract can be obtained, specifically, the desired material, its dried and processed products, etc. are immersed in the solvent, and then methods such as cold extraction at room temperature, heating extraction, ultrasonic extraction using ultrasonic waves, and reflux extraction using a reflux condenser may be used.

The *Acanthopanax* extract that can be applied to the *Acanthopanax* extract is commercially sold, but it can be used without limitation that it is collected or cultivated in nature. In addition, the *Acanthopanax* can be used without limitation in parts such as flowers, leaves, fruits, seeds, roots or stems. In addition, it is most preferable to use those harvested in May to June in terms of improving the antidiabetic or antiobesity effect.

*Acanthopanax* is a shrub plant belonging to Araliaceae, and its leaves are divided into five. There are 15 species in Korea, including such as *Acanthopanax senticosus* (RUPR. et MAX.) HARMS, *Acanthopanax sessiliflorus* (RUPR. et MAX.) SEEM., and *Acanthopanax senticosus* var. *subinermis* KITAGAWA as a type of *Acanthopanax*. Long ago, in oriental medicine, it was classified as a medicine that has no toxicity and side effects, and the roots and woody parts (eggplants) have been used as medicines and leaves, fruits and flowers can also be used as medicinal parts. Chiisanoside is contained in the leaves of *Acanthopanax*, and Acanthoside B and D, which are the glycosides of *Acanthopanax*, as well as sylrgin and coumarin glycosides are contained in the root. In addition, *Acanthopanax* contains water-soluble polysaccharides that enhance immunity. *Acanthopanax* is known to have a spicy, bitter, and warm nature, and to act on liver cirrhosis and nerves to eliminate customs, boost energy, and call essence. In addition, it is known to compensate for sickness caused by weakness of the five organs and seven symptoms caused by weakness in men, and to be used for inability to use the legs, to enhance the body's energy, to improve stamina, to clear the mind, to increase willpower, to make the body light and prevent aging, and to clear and clean the bad blood in the body, and it is known to treat various symptoms such as pain in the back spine, male genital warts, genital warts, and female eumgyeong syndrome.

In the present invention, the species is not particularly limited as long as it is a plant of the genus *Acanthopanax*, and non-limiting examples thereof include *Acanthopanax sessiliflorus* (RUPR. et MAX.) SEEM., *Acanthopanax senticosus* (RUPR. et MAX.) HARMS, *Acanthopanax senticosus* var. *subinermis* KITAGAWA, *Acanthopanax chi-* isanense NAKAI, *Acanthopanax koreanum* NAKAI (*Acanthopanax rufinerve* NAKAO, *Acanthopanax seoulense* NAKAI, *Acanthopanax sieboloians* and *Acanthopanax sieboldianum* MAKINO. In the present invention, the *Acanthopanax* extract may be a single or mixed extract of the aforementioned Plant of the genus *Acanthopanax*, and preferably may be *Acanthopanax sessiliflorus* (RUPR. et MAX.) SEEM extract.

For example, the *Acanthopanax* extract can be obtained by treating *Acanthopanax* leaves with a solvent of methanol or ethanol. The concentration range of the solvent may be 20% to 100%, 30% to 90%, or 50% to 70%, and the extraction efficiency is the best when the concentration of the solvent is 55% to 65%, preferably 60%.

Specifically, the solvent treatment may be performed for 1 to 10 hours, 3 to 7 hours, or 4 to 6 hours and the extraction temperature is 30° C. to 90° C., 40° C. to 80° C., 50° C. to 70° C., preferably 60° C. After solvent treatment, the process of sonication at room temperature for 15 minutes may be repeated 1 to 5 times or 3 times for extraction. Thereafter, centrifugation at 4,500 rpm for 5 minutes, filtration, and vacuum concentration may be performed.

Chiisanogenin can be separated from the *Acanthopanax* extract by performing open column chromatography (N.P). Solvents used for open column chromatography include hexane and acetone, and the ratio of hexane and acetone may be 4:1 to 1:1 (WN). At this time, the purity of the separated chiisanogenin is 90, 91, 92, 95 or 97% or more.

In the present invention, the chiisanogenin is a compound having the structure of Formula 1 below:

[Formula 1]

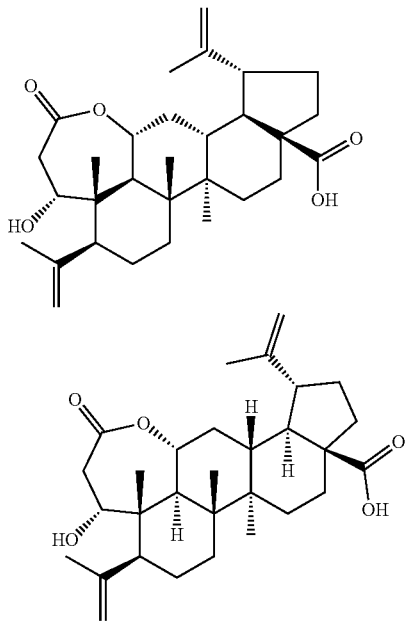

In the present invention, the chiisanogenin may be isolated from plant extracts of the genus *Acanthopanax* or fractions thereof, purchased commercially and used, or prepared by chemical synthesis methods known in the art.

In the present invention, the chiisanogenin includes not only the compound of Formula 1, but also pharmaceutically acceptable salts thereof, possible solvates, hydrates, racemates, and stereoisomers that can be prepared therefrom.

The term "chiisanogenin derivative" in the present invention includes, compounds having the same molar structure as chiisanogenin or glycosides, which are effective in improving liver diseases, but are not limited thereto, examples may include chiisanoside, 22-alpha-hydrochisanoside, and 22-alpha-hydroxanogenin, and the like.

Meanwhile, *Garcinia cambogia* has been used as a souring agent for pork and fish and as a spice for curries for centuries in India and southern Asia, and *Garcinia cambogia* extract is used as an auxiliary ingredient (minimum amount of 5% or less should be used, but daily intake cannot exceed 6 g) in formula foods for weight control according to the 'Food Code' in Korea. In addition, in foreign countries such as the United States, it is sold as a dietary supplement or food ingredient at an intake level of 500 to 4500 mg/day. *Garcinia cambogia* intake has been reported to cause acute liver toxicity in some consumers, so special attention is required for the dosage and administration cycle.

In one embodiment of the present invention, in order to reduce the risk of liver toxicity of the above-mentioned *Garcinia cambogia* while utilizing the excellent weight control effect, a combination therapy with a *Acanthopanax* extract was attempted. As a result, it was confirmed that a synergistic effect was shown in the anti-diabetic and anti-obesity effects in the combination therapy of *Garcinia cambogia* extract and *Acanthopanax* extract.

In the *Garcinia cambogia* extract, various organs (e.g. leaves, roots, stems, branches, tender branches, skins, fruit skins and seeds, etc.) of *Garcinia cambogia* can be used, and preferably leaves, tender branches, stems, branches, peels, peels or roots of fruits can be used.

In this case, commercially available *Garcinia cambogia* extract raw materials may be used as the *Garcinia cambogia* extract. For example, *Garcinia cambogia* extract sold by Sabinsa Korea Corporation can be used.

In addition, HCA may be separated from the *Garcinia cambogia* extract by a conventional extraction method, or commercially available HCA may be used. For example, HCA sold by Chromadex may be used. At this time, the purity of HCA is 90, 91, 92, 95 or 97% or more.

In one embodiment of the present invention, when the composition includes the *Garcinia cambogia* extract and the *Acanthopanax* extract as active ingredients, the composition can be prepared by preparing the *Garcinia cambogia* extract and the *Acanthopanax* extract and then mixing them, alternatively, the composition may be prepared by preparing an extract after mixing *Garcinia cambogia* and *Acanthopanax*.

As used herein, the term "diabetes" refers to a disease that occurs when the secretion of insulin is insufficient or the action and function of insulin are not sufficiently achieved. In this disease, excessive breakdown of glycogen, protein, and fat causes an abnormal increase in glucose concentration in the liver or blood, resulting in diabetes and ketonuria, and abnormalities in water and electrolyte metabolism lead to pathological conditions such as circulatory disorders and renal disorders, along with blood concentration due to loss of electrolytes. Diabetes is divided into insulin-dependent diabetes mellitus (type I) and non-insulin-dependent diabetes mellitus (type II). Diagnosis of diabetes is generally possible through the measurement of blood glucose concentration, which shows differences according to criteria. In humans, diabetes is generally diagnosed when the blood glucose level is 200 mg/dl or more at normal times and 140 mg/dl or more when fasting.

As used herein, the term "obesity" refers to a state in which body fat is excessively accumulated. The criterion for obesity can be said to be obese if the body fat is 25% or more of body weight, and women are 30 to 35% or more, body mass index (BMI) expressed as weight (kg)/height (m)$^2$ is widely used as a general measurement method. Westerners are defined as obesity if their body mass index exceeds 30 kg/m$^2$ and overweight if it is between 25 and 30 kg/m$^2$, and in the case of Asians, 28 kg/m$^2$, which is 2 degrees lower than this, is considered obese, and 23 to 28 kg/m$^2$ is considered overweight. In addition, obesity can be defined based on the waist to hip ratio (WHR) or the amount of abdominal fat, and all cases of obesity defined by conventional criteria other than the above criteria are included in the present invention.

According to one embodiment of the present invention, a composition comprising a *Acanthopanax* extract and a *Garcinia cambogia* extract, a composition comprising a *Acanthopanax* extract and HCA, a composition comprising chiisanogenin and a *Garcinia cambogia* extract, or a composition comprising chiisanogenin and HCA has excellent antidiabetic activity and antiobesity activity, so it can be widely applied as a material for functional foods and feeds, as well as pharmaceutical compositions for preventing and treating diabetes and obesity.

In particular, considering that *Garcinia cambogia* extract can cause liver toxicity, the composition of the present invention obtained by combining the extract of *Garcinia cambogia* with the *Acanthopanax* extract or chiisanogenin may exhibit a desired effect of preventing or treating obesity or diabetes even when administered at a dose that does not cause side effects or has a very low possibility of side effects in each substance Specifically, the first component and the second component may be included in a weight ratio of 5:1 to 1:20. More specifically, it may be included in a weight ratio of 4.5:1 to 1:18, 4:1 to 1:15, 3:1 to 1:9, 3:1 to 1:6, 2:1 to 1:4, or 1:1 to 3:1. When mixed and used at a weight ratio within the above range, a clear synergistic effect can be exhibited compared to single use in antidiabetic and antiobesity effects.

In addition, the first component may be chiisanogenin, and the second component may be a *Garcinia cambogia* extract. In this case, the first component and the second component may be included in a weight ratio of 1:1 to 1:9, 1:1 to 1:5, or about 1:3.

In addition, the first component may be an *Acanthopanax* extract, and the second component may be HCA. In this case, the first component and the second component may be included in a weight ratio of 5:1 to 1:1, 4:1 to 1:1, or 4:1 to 3:1. It was confirmed that when the two components were used in combination within the above range, the antidiabetic effect was superior to that when each component was treated alone.

In addition, the *Garcinia cambogia* extract containing 40 to 90%, 50 to 80%, or 60% to 70% of HCA may be used.

In addition, the first component may be chiisanogenin, and the second component may be HCA. In this case, the first component and the second component may be included in a weight ratio of 1:50 to 50:1, 1:45 to 45:1, 1:40 to 40:1, 1:35 to 35:1, 1:30 to 30:1, 1:25 to 25:1, 1:20 to 20:1, 1:15 to 15:1, 1:10 to 10:1, 1:9 to 9:1, 1:8 to 9:1, 1:7 to 9:1, 1:6 to 9:1, 1:5 to 9:1, 1:4 to 9:1, 1:3 to 9:1 or 2:3 to 9:1.

Preferably, the pharmaceutical composition may include chiisanogenin and HCA in a weight ratio of 1:6 to 1:1.

Preferably, the pharmaceutical composition may include chiisanogenin and HCA in a weight ratio of 1:4 to 1:1.

In addition, the first component may be a *Acanthopanax* extract, and the second component may be a *Garcinia cambogia* extract. In this case, the first component and the second component may be included in a weight ratio of 2:1 to 1:2.

In one embodiment of the present invention, chiisanogenin and HCA may be mixed at a weight ratio of 4:6 to 6:4 to exhibit superior anti-obesity and anti-diabetic effects than when each component is treated alone.

In the pharmaceutical composition according to the present invention, the first component and the second component may be administered simultaneously, separately or sequentially. For example, when each component comprised in the pharmaceutical composition of the present invention is a single composition, it can be administered simultaneously, if not in a single composition, one component may be administered before, after, and/or concurrently with the other components. The order of administration of the pharmaceutical composition according to the present invention, that is, whether to administer something simultaneously, separately or sequentially at any time point can be determined by a doctor or expert. This order of administration can vary depending on many factors.

In addition, the pharmaceutical composition may comprise a pharmaceutically acceptable carrier. The composition comprising a pharmaceutically acceptable carrier may be in various oral or parenteral formulations. When formulated, it is prepared using diluents or excipients such as commonly used fillers, extenders, binders, wetting agents, disintegrants, and surfactants.

In addition, the pharmaceutical composition may have any one formulation selected from the group consisting of powders, granules, tablets, capsules, suspensions, emulsions, syrups, aerosols, external preparations, suppositories and injections.

Specifically, solid preparations for oral administration include tablets, pills, powders, granules, capsules, etc. and these solid preparations are prepared by mixing one or more compounds with at least one or more excipients, such as starch, calcium carbonate, sucrose or lactose, and gelatin. In addition to simple excipients, lubricants such as magnesium stearate and talc may also be used. Liquid preparations for oral administration include suspensions, solutions for internal use, emulsions, and syrups, and in addition to water and liquid paraffin, which are commonly used simple diluents, various excipients such as wetting agents, sweeteners, aromatics, and preservatives may be included.

Formulations for parenteral administration include sterilized aqueous solutions, non-aqueous solvents, suspensions, emulsions, freeze-dried formulations, and suppositories. Propylene glycol, polyethylene glycol, vegetable oils such as olive oil, and injectable esters such as ethyl oleate may be used as non-aqueous solvents and suspending agents. As a base material for suppositories, witepsol, macrogol, tween 61, cacao paper, laurin paper, glycerogelatin, etc. may be used.

The administration route of the composition may be administered through any general route as long as it can reach the target tissue. The pharmaceutical composition may be administered intraperitoneally, intravenously, intramuscularly, subcutaneously, intradermally, orally, intranasally, intrapulmonary, intrarectally, as desired, but is not limited thereto. In addition, the composition may be administered by any device capable of transporting an active substance to a target cell.

The dosage of the composition of the present invention may vary depending on the patient's body weight, age, gender, health status, diet, administration time, administration method, excretion rate and disease severity, and the like.

The pharmaceutical composition of the present invention may further include pharmaceutically acceptable additives, at this time, starch, gelatinized starch, microcrystalline cellulose, povidone, colloidal silicon dioxide, calcium hydrogen phosphate, lactose, mannitol, candy, arabic gum, pregelatinized starch, corn starch, powdered cellulose, hydroxypropyl cellulose, opadry, sodium starch glycolate, carnauba wax lead, synthetic aluminum silicate, stearic acid, magnesium stearate, aluminum stearate, calcium stearate, white sugar, dextrose, sorbitol and talc and the like may be used as pharmaceutically acceptable additives. A pharmaceutically acceptable additive according to the present invention may be included in an amount of 0.1 to 90 parts by weight based on the composition, but is not limited thereto.

Another aspect of the present invention is to provide a food composition for preventing or alleviating diabetes or obesity, comprising a first component of *Acanthopanax* extract, chiisanogenin, or chiisanogenin derivative, and a second component of *Garcinia cambogia* extract or hydroxy citric acid (HCA).

The food composition can be used as a food because the first component and the second component are substances safe for the human body and are effective in preventing or improving diabetes or obesity even when ingested. At this time, for the *Acanthopanax* extract, chiisanogenin, *Garcinia cambogia* extract, and HCA included in the food composition, the contents described above in the pharmaceutical composition are referred to.

In the food according to the present invention, the complex extract of the present invention is added as it is, or additives such as common flavoring agents and preservatives may be further included in other types of foods, health functional foods, or beverages.

The food of the present invention can be prepared in the form of a powder, granule, tablet, capsule, pill or liquid solution according to a known manufacturing method and used as food, beverage, gum, tea, vitamin complex, health supplements. The content of the extract according to the present invention can be adjusted to 0.0001 to 100% by weight based on the total weight of the food composition depending on the formulation. There is no particular limitation on other ingredients except for containing the extract according to the present invention as an active ingredient, and various common flavoring agents or natural carbohydrates may be included as additional components.

Examples of the natural carbohydrates are common sugars for example, monosaccharides such as glucose, fructose, and the like; disaccharides such as maltose, sucrose and the like; and polysaccharides such as dextrins, cyclodextrins, and the like, and sugar alcohols such as xylitol, sorbitol, and erythritol. As flavoring agents other than those mentioned above, natural flavoring agents (thaumatine, stevia extract (e.g. rebaudioside A, glycyrrhizin, etc.) and synthetic flavoring agents (saccharin, aspartame, etc.) can advantageously be used.

In addition to the above, the composition of the present invention may comprise various nutrients, vitamins, minerals (electrolytes), flavors such as synthetic flavors and natural flavors, colorants and enhancers (cheese, chocolate, etc.), pectic acid and its salts, alginic acid and its salts, organic acids, protective colloidal thickeners, pH adjusters, stabilizers, preservatives, glycerin, alcohol, carbonation agents used in carbonated beverages, and the like.

Another aspect of the present invention is to provide a feed composition for preventing or alleviating diabetes or obesity, comprising a first component of *Acanthopanax* extract, chiisanogenin, or chiisanogenin derivative, and a second component of *Garcinia cambogia* extract or hydroxy citric acid (HCA).

The feed composition according to the present invention may be further with the additives and the like added to the complex extract of the present invention as it is, or to other types of feed compositions. At this time, for the *Acanthopanax* extract, chiisanogenin, *Garcinia cambogia* extract, and HCA comprised in the food composition, the contents described above in the pharmaceutical composition are referred to.

The present invention provides use of a first component of *Acanthopanax* extract, chiisanogenin, or chiisanogenin derivative, and a second component of *Garcinia cambogia* extract or hydroxy citric acid (HCA) for preparing an agent for the treating of diabetes or obesity.

The present invention provides a method of treating diabetes or obesity comprising administering an effective amount of a composition containing a first component of *Acanthopanax* extract, chiisanogenin, or chiisanogenin derivative, and a second component of *Garcinia cambogia* extract or hydroxy citric acid (HCA) to a subject in need thereof.

The 'effective amount' of the present invention refers to an amount that, when administered to a subject, has an effect of improving, treating, preventing, detecting, diagnosing, or inhibiting or reducing diabetes or obesity, and the 'subject' may be an animal, preferably an animal, including a mammal, particularly a human, and may be an animal-derived cell, tissue, organ, or the like. The subject may be a patient in need of the effect.

The 'treatment' of the present invention comprehensively refers to improving diabetes or obesity or the symptoms of the disease, this may include curing, substantially preventing, or improving the condition of cancer and cancer metastasis or immune cell migration related diseases, and it includes, but is not limited to, alleviating, curing, or preventing one symptom or most of the symptoms resulting from the disease.

As used herein, the term "comprising" is used synonymously with "containing" or "being characterized", and does not exclude additional ingredients or steps not mentioned in the composition or method. The term "consisting of" means excluding additional elements, steps, or ingredients not otherwise specified. The term "essentially consisting of" means including the mentioned elements or steps as well as any element or step that does not substantially affect basic characteristics of the mentioned elements or steps in the scope of compositions or methods.

Hereinafter, the present invention will be described in more detail by the following examples. However, the following examples are only for exemplifying the present invention, and the scope of the present invention is not limited only to these.

Example 1. Preparation of *Acanthopanax* Extract and Chiisanogenin Isolated Therefrom Example 1.1. Preparation of *Acanthopanax* Extract 3 g of the crushed *Acanthopanax* leaves (Scientific name: *Eleutherococcus sessiliflorus* (Rupr. & Maxim.), Voucher number: KRIB 0079085-0079086, Obtained from: Suxinmyeon, Cheonan-si, Chungcheongnam-do) were put in a bottle, 100 mL of a solvent corresponding to the above solvent conditions was added, extracted for 5 hours under the following temperature conditions in a water bath, and then cooled at room temperature for 1 hour. After filtering on filter paper (advantec NO.2, 5 μm), the mixture was concentrated, and 30 mL of 50% (30, 60° C. sample) and 100% MeOH (90° C. sample) solvent was precisely measured to completely dissolve the extract, and the extract was repeatedly extracted once in the same manner, and analyzed by UPLC after filtering (advantec, 0.2 μm) with a syringe. Response surface analysis was performed using the obtained extract (30 mg/mL).

9 kinds of extracts were finally obtained by varying the ethanol concentration (30%, 60%, 90%) and extraction temperature (30° C., 60° C., 90° C.), and its chiisanogenin content was confirmed for the dried raw material and shown in FIG. 1.

Referring to FIG. 1, it can be seen that the content of chiisanogenin in the raw material appears high under specific extraction conditions. In particular, it can be seen that the extraction temperature condition of 60° C. raises the chiisanogenin content the most in all concentrations of ethanol solvents. In addition, as a result of statistical analysis of response standard analysis using minitab 18 (Eretec Inc), it was confirmed that 60% ethanol at 60° C. was the optimal condition.

Example 1.2. Separation of Chiisanogenin, an Indicator Component of the *Acanthopanax* Extract Solvent extraction was repeatedly performed 3 times for 3 days at 30° C. using 80% methanol for 15.0 kg of the *Acanthopanax* leaves. 2.9 kg of the extract was subjected to open column chromatography (N.P.) to obtain 4 fractions (fr1 to fr4). The solvent used at this time was hexane:acetone in a ratio of 4:1 to 1:1 (W/V). Of the 4 fractions, fr.2 (28.38 g) was subjected to open column chromatography using hexane:acetone as a 4:1 (W/N) solvent to obtain 2 small fractions.

In order to analyze the fractions, components of the fractions were analyzed using an ACQUITY™ UPLC (Ultra Performance Liquid Chromatography) and a CAD detector (Charged Aerosol Detector). At this time, 0.1% FA (Formic acid)/D.W was used as solvent A, and 0.1% FA/ACN (acetonitrile) solvent was used as solvent B, and the analysis was performed under the gradient conditions shown in Table 1 below. In addition, analysis was performed under the CAD conditions shown in Table 2 below.

TABLE 1

| Time(min) | Flow(ml/min) | % A | % B |
|---|---|---|---|
| 0.00 | 0.400 | 90 | 10 |
| 1.20 | 0.400 | 90 | 10 |
| 3.00 | 0.400 | 70 | 30 |
| 4.00 | 0.400 | 65 | 35 |
| 9.00 | 0.400 | 30 | 70 |
| 11.00 | 0.400 | 0 | 100 |
| 13.10 | 0.400 | 0 | 100 |
| 13.20 | 0.400 | 90 | 10 |
| 15.00 | 0.400 | 90 | 10 |

TABLE 2

| Division | Condition |
|---|---|
| Filter | 2.0 |
| Data Rate | 20 Hz |

ACQUITY UPLC BEH C18 1.7 μm, 2.1×100 mm was used as the column. 5 μl of the extract was used at a concentration of 1 mg/ml.

Example 2. Confirmation of the Chiisanogenin Content of Extracts from the *Acanthopanax* Leaves According to Harvest Time In order to determine the harvesting time of the *Acanthopanax* leaves with the highest chiisanogenin content, chiisanogenin was isolated from the *Acanthopanax* leaves harvested from July 2016 to June 2019 using the extraction method used in Example 1.2 and compared and analyzed. The content of chiisanogenin in the leaf extract of *Acanthopanax* for each harvest time is shown in FIG. 4.

Figure 4:
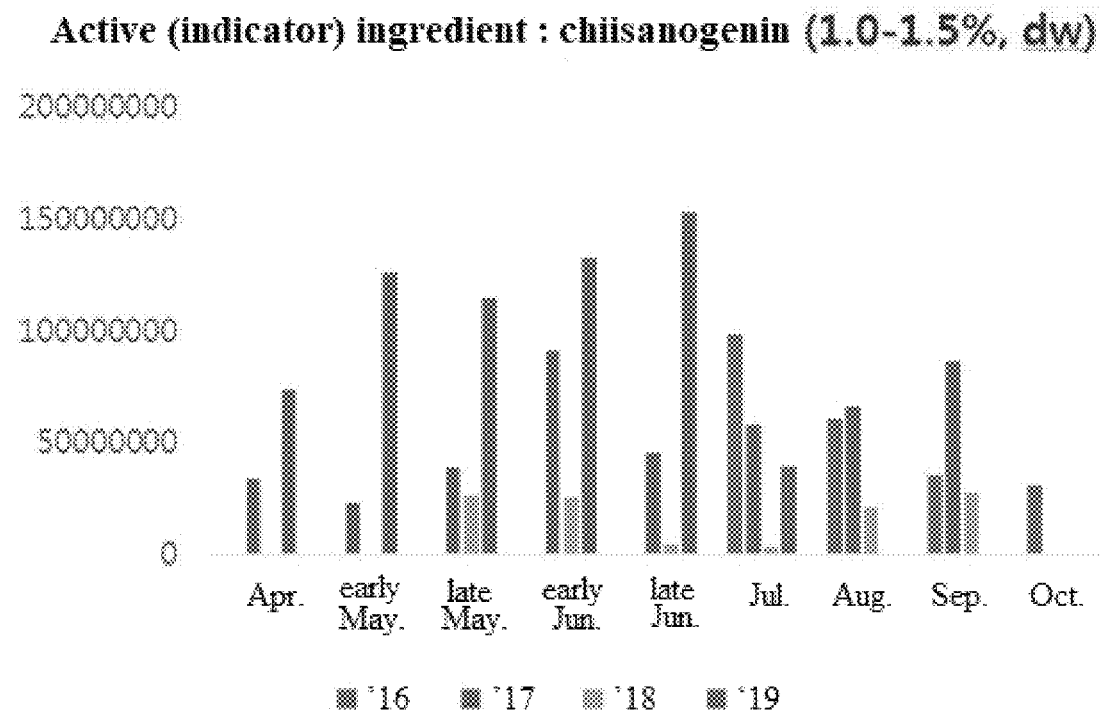
FIG. 4 shows the results of analysis of the chiisanogenin content of the leaf extract of *Acanthopanax* at each harvest time.

Referring to the results of FIG. 4, the content of chiisanogenin was found to be the highest in the *Acanthopanax* leaves harvested in May or June.

Example 3. Preparation of *Garcinia cambogia* Extract

*Garcinia cambogia* extract was used as a raw material (Batch No. C150292E) distributed by Sabinsa Korea Corporation, and HCA was purchased from Chromadex (ASB-00008387-250).

Example 4. Confirmation of Cytotoxicity of *Acanthopanax* Extract, Chiisanogenin, *Garcinia cambogia* Extract and Hydroxy Citric Acid (HCA)

DMEM medium (Gibco) supplemented with 10% Bovine Calf Serum and 1% Penicillin-streptomycin was used as a growth media (GM) to culture 3T3-L1 cells, which are mouse preadipocytes. The suspension was suspended at a concentration of $2 \times 10^3$ cells/ml, and 100 μl each was inoculated into a 96-well plate, and the cells were cultured to full capacity for 3 days. In order to induce fat differentiation, DMEM medium containing 10% FBS was replaced with a differentiation media (DM) supplemented with insulin, dexamethasone and 3-isobutyl-1-methylxanthine (IBMX), and cultured for 2 days. After 2 days, DMEM medium containing 10% FBS containing insulin was added to the existing medium. In order to confirm the effect of the drug during the adipocyte differentiation, the drug was treated together when the medium was exchanged. The drug used at this time was a chiisanogenin compound isolated from *Acanthopanax* extract, *Garcinia cambogia* extract (notified raw material, 60% HCA), Ca-HCA, and *Acanthopanax* extract. As described in the CCK-8 (Dojindo) kit for counting cells, 10 μl of CCK-8 solution was mixed with 90 μl of medium and added at 100 μl per well. After reacting for at least 30 minutes to 1 hour, absorbance was measured at 450 nm.

Cell viability was calculated according to Math Formula 1 below, with the negative control treated with 0.1% DMSO as 100%, and the results are shown in Tables 3 to 5 below.

[Math Formula 1]
$$\text{Cell Viability (\%)} = \frac{\text{Extract treatment group } OD \text{ 450 nm value}}{\text{Negative Control group } OD \text{ 450 nm value}} \times 100$$

TABLE 3

| No. | GM | DM | Garcinia cambogia extract | Chiisanogenin | Cell Viability (%, Mean ± Deviation) |
|---|---|---|---|---|---|
| | | | Mixture Ratio | | |
| 1 | + | − | 0 | 0 | 65.67 ± 5.08 |
| 2 | − | + | 0 | 0 | 100.00 ± 14.60 |
| 3 | − | + | 10 (50 µg/mL) | 0 | 106.40 ± 7.19 |
| 4 | − | + | 9 | 1 | 108.54 ± 5.08 |
| 5 | − | + | 8 | 2 | 107.41 ± 8.33 |
| 6 | − | + | 7 | 3 | 105.73 ± 5.03 |
| 7 | − | + | 6 | 4 | 104.62 ± 7.14 |
| 8 | − | + | 5 | 5 | 97.99 ± 2.91 |
| 9 | − | + | 4 | 6 | 102.90 ± 10.68 |
| 10 | − | + | 3 | 7 | 101.56 ± 9.47 |
| 11 | − | + | 2 | 8 | 103.62 ± 10.69 |
| 12 | − | + | 1 | 9 | 111.31 ± 6.65 |
| 13 | − | + | 0 | 10 (25 µg/mL) | 102.64 ± 10.09 |

TABLE 4

| No. | GM | DM | Garcinia cambogia extract | Chiisanogenin | Cell Viability (%, Mean ± Deviation) |
|---|---|---|---|---|---|
| | | | Density (µg/mL) | | |
| 1 | + | − | 0 | 0 | 80.28 ± 3.18 |
| 2 | − | + | 0 | 0 | 100.00 ± 9.01 |
| 3 | − | + | 40 | 0 | 110.41 ± 13.15 |
| 4 | − | + | 60 | 20 | 105.62 ± 10.42 |
| 5 | − | + | 30 | 10 | 125.93 ± 12.35 |
| 6 | − | + | 0 | 10 | 127.27 ± 18.60 |

TABLE 5

| No. | Sample | Density (µg/mL) | Cell Viability (%, Mean ± Deviation) |
|---|---|---|---|
| 1 | Negative Control | 0 | 100.00 ± 2.15 |
| 2 | Garcinia cambogia extract | 12.5 | 114.62 ± 6.37 |
| | | 25 | 116.46 ± 11.17 |
| | | 50 | 99.00 ± 2.28 |
| | | 100 | 93.12 ± 3.01 |
| 3 | Acanthopanax extract | 12.5 | 97.64 ± 1.77 |
| | | 25 | 87.39 ± 4.85 |
| | | 50 | 84.14 ± 4.09 |
| | | 100 | 73.92 ± 14.87 |
| 4 | Ca-HCA | 12.5 | 113.20 ± 14.37 |
| | | 25 | 115.37 ± 8.86 |
| | | 50 | 86.24 ± 8.74 |
| | | 100 | 88.65 ± 11.58 |
| 5 | Chiisanogenin | 12.5 | 106.41 ± 3.40 |
| | | 25 | 106.06 ± 3.22 |
| | | 50 | 117.77 ± 9.59 |
| | | 100 | 104.31 ± 9.72 |

Referring to Tables 3 to 5 above, it can be seen that the active ingredients of the present invention, *Garcinia cambogia* extract, *Acanthopanax* extract, hydroxy citric acid (HCA), and chiisanogenin, do not significantly affect cell viability, and therefore are not cytotoxic.

Example 5. Confirmation of Fat Accumulation Inhibitory Effect According to Combined Treatment of *Garcinia cambogia* Extract, *Acanthopanax* Extract or Chiisanogenin 3T3-L1 cells, which are preadipocytes of mice, are suspended at a concentration of $2 \times 10^4$ cells/ml using Dulbecco's Modified EaDCRT media (DMEM, Gibco) containing 10% of Bovine Calf Serum as a growth media (GM), and then inoculated into 24-well plates at 1 ml each, and then adipocytes were cultured for 3 days to become confluent. In order to induce adipocyte differentiation, DMEM media containing 10% FBS was replaced with differentiation media (DM) supplemented with insulin, dexamethasone and 3-isobutyl-1-methylanthin (IBMX) and cultured for 2 days. After 2 days, DMEM media containing 10% FBS containing insulin was added to the existing medium. In order to confirm the effect of the drug during the adipocyte differentiation, the drug was treated together when the medium was replaced. In order to measure lipid accumulation after inducing the adipocyte differentiation, it was measured using Oil red 0 staining analysis (Sigma-aldrich). To fix the cells, 1% formaldehyde (based on distilled water) was added and reacted at 4° C. for 1 hour, followed by washing with distilled water, and then stained with 500 µl of filtered Oil Red 0 solution at room temperature for 1 hour. Then, after washing with distilled water, 300 µl of 100% isopropyl alcohol was added to extract intracellular oil red 0, and the degree of color development was measured at 492 nm using a microplate measuring instrument. The inhibition rate was calculated according to Math Formula 2 below with the positive control as 100%, and the results are shown in Tables 6 and 7 below.

In order to determine the statistically significant variance between each group, it was analyzed using one-way ANOVA, and the displayed result values were marked to #p<0.05, ##p<0.01, and ###p<0.001 through comparison with the GM group, and *p<0.05, p<0.01, and *p<0.001 through comparison with the DM group as statistically significant.

Relative Fat Accumulation Inhibition Rate (%) = [Math Formula 2]

$$\left\{ 1 - \frac{\text{(Drug treatment group \%} - \text{Negative Control group \%)}}{\text{(Positive Control group \%} - \text{Negative Control group \%)}} \right\} \times 100$$

TABLE 6

| No. | GM | DM | Garcinia cambogia extract | Chiisanogenin | Fat Accumulation Rate (% relative to positive control, mean ± deviation) | Inhibition Rate (%, mean ± deviation) |
|---|---|---|---|---|---|---|
| | | | Mixture Ratio | | | |
| 1 | + | − | 0 | 0 | 43.37 ± 0.77 | — |
| 2 | − | + | 0 | 0 | 100.00 ± 6.21 # | — |
| 3 | − | + | 10 | 0 | 95.20 ± 3.15 * | 15.55 ± 5.56 |

TABLE 6-continued

| No. | GM | DM | Garcinia cambogia extract | Chiisanogenin | Fat Accumulation Rate (% relative to positive control, mean ± deviation) | Inhibition Rate (%, mean ± deviation) |
|---|---|---|---|---|---|---|
| | | | (50 µg/mL) | | | |
| 4 | − | + | 9 | 1 | 86.01 ± 5.53 ** | 24.71 ± 7.89 |
| 5 | − | + | 8 | 2 | 84.46 ± 2.04 ** | 27.44 ± 1.70 |
| 6 | − | + | 7 | 3 | 82.74 ± 4.54 * | 30.48 ± 7.43 |
| 7 | − | + | 6 | 4 | 75.02 ± 1.29 ** | 44.11 ± 3.47 |
| 8 | − | + | 5 | 5 | 80.41 ± 1.27 ** | 34.59 ± 2.24 |
| 9 | − | + | 4 | 6 | 81.21 ± 2.86 ** | 33.18 ± 3.11 |
| 10 | − | + | 3 | 7 | 82.17 ± 4.95 * | 31.49 ± 6.86 |
| 11 | − | + | 2 | 8 | 82.40 ± 0.78 * | 31.08 ± 2.78 |
| 12 | − | + | 1 | 9 | 85.46 ± 1.60 * | 25.68 ± 2.52 |
| 13 | − | + | 0 | 10 | 87.21 ± 4.82 ** | 22.59 ± 7.34 |
| | | | (25 µg/mL) | | | |

TABLE 7

| No. | GM | DM | Garcinia cambogia extract | Chiisanogenin Density (µg/mL) | Fat Accumulation Rate (% relative to positive control, mean ± deviation) | Inhibition Rate (%, mean ± deviation) |
|---|---|---|---|---|---|---|
| 1 | + | − | 0 | 0 | 56.87 ± 2.52 | — |
| 2 | − | + | 0 | 0 | 100.00 ± 4.38 # | — |
| 3 | − | + | 40 | 0 | 94.85 ± 4.64 | 11.94 ± 1.06 |
| 4 | − | + | 30 | 10 | 81.65 ± 4.84 ** | 42.55 ± 3.91 |
| 5 | − | + | 60 | 20 | 73.47 ± 3.99 * | 61.52 ± 3.42 |
| 6 | − | + | 0 | 10 | 95.13 ± 5.90 | 11.29 ± 1.47 |

Referring to Tables 6 and 7, it can be seen that when the *Garcinia cambogia* extract and chiisanogenin were mixed and treated, the fat accumulation rate was statistically significantly reduced compared to the case of the single substance treatment. In particular, it can be seen that the fat accumulation inhibitory effect is the highest when mixed at a weight ratio of about 3:1.

Example 6. Confirmation of Triglyceride Production Inhibitory Effect of *Garcinia cambogia* Extract, *Acanthopanax* Extract, HCA, and Chiisanogenin 3T3-L1 cells, which are preadipocytes of mice, are suspended at a concentration of $2\times10^4$ cells/ml using Dulbecco's Modified EaDCRT media (DMEM, Gibco) containing 10% of Bovine Calf Serum as a growth media (GM), and then inoculated into 24-well plates at 1 ml each, and then adipocytes were cultured for 3 days to become confluent. In order to induce adipocyte differentiation, DMEM media containing 10% FBS was replaced with differentiation media (DM) supplemented with insulin, dexamethasone and 3-isobutyl-1-methylanthin (IBMX) and cultured for 2 days. After 2 days, DMEM media containing 10% FBS containing insulin was added to the existing medium. In order to confirm the effect of the drug during the adipocyte differentiation, the drug was treated together when the medium was replaced. After differentiation was induced under the same conditions as above, triglyceride (TG) produced was measured using an Adipogenesis Colorimetric Assay (Biovision) kit. According to the protocol provided in the kit, after washing the cells once with PBS, 100 µl of Lipid Extract solution was added to scrape the cells, and the cells were placed at 90° C. for 30 minutes. Thereafter, the supernatant, which had turned cloudy, was left at room temperature until it became transparent, and then 50 µl of the supernatant was obtained and transferred to a 96-well plate. After adding 2 µl of lipase and reacting for 10 minutes, 50 µl of the reaction mixture containing the probe and enzyme mix was added and reacted, and the degree of color development was measured at 570 nm with a microplate meter. The concentration of triglyceride produced in the cells was determined using a standard curve for each concentration according to the triglyceride sample included in the kit. The inhibition rate was calculated according to Math Formula 3 below with the positive control as 100%, and the results are shown in Tables 8 and 9 below.

In order to determine the statistically significant variance between each group, it was analyzed using a student t-test, and the displayed result value were marked to #p<0.001 through comparison with the GM group, and *p<0.05, p<0.01, and *p<0.001 through comparison with the DM group, as statistically significant.

[Math Formula 3]
$$TG \text{ inhibition rate } (\%) = \left\{ 1 - \frac{\text{(Drug treatment group \% − Negative Control group \%)}}{\text{(Positive Control group \% − Negative Control group \%)}} \right\} \times 100$$

TABLE 8

| No. | GM | DM | Garcinia cambogia extract Density (μg/mL) | Chiisanogenin | TG Production Rate (% relative to positive control, mean ± deviation) | Inhibition Rate (%, mean ± deviation) |
|---|---|---|---|---|---|---|
| 1 | + | − | 0 | 0 | 19.85 ± 4.31 | — |
| 2 | − | + | 0 | 0 | 100.00 ± 6.86 # | — |
| 3 | − | + | 40 | 0 | 64.71 ± 7.67 ** | 47.77 ± 8.06 |
| 4 | − | + | 30 | 10 | 53.85 ± 1.72 *** | 57.58 ± 5.67 |
| 5 | − | + | 60 | 20 | 38.43 ± 2.13 *** | 76.82 ± 4.60 |
| 6 | − | + | 0 | 10 | 90.84 ± 4.21 | 11.43 ± 5.34 |

TABLE 9

| No. | Sample | Density (μg/mL, ratio) | Differentiation induction medium | TG Production Rate (% relative to positive control) | Inhibition Rate (%) | Note |
|---|---|---|---|---|---|---|
| 1 | Negative control | 0 | − | 17.06 ± 0.54 | — | |
| 2 | Positive control | 0 | + | 100.00 ± 2.92 | — | |
| 3 | Garcinia cambogia extract | 25 | + | 74.65 ± 0.93 | 30.56 ± 1.12 | |
| | | 50 | + | 72.90 ± 0.35 | 32.67 ± 0.42 | |
| 4 | Acanthopanax extract | 25 | + | 97.56 ± 0.55 | 4.08 ± 0.92 | |
| | | 50 | + | 86.10 ± 1.58 | 16.76 ± 7.49 | |
| 5 | Chiisanogenin | 25 | + | 94.63 ± 0.61 | 6.47 ± 0.73 | |
| | | 50 | + | 81.07 ± 0.20 | 22.82 ± 0.25 | |
| 6 | Ca-HCA | 25 | + | 94.51 ± 0.81 | 6.62 ± 0.98 | |
| | | 50 | + | 90.54 ± 0.73 | 11.41 ± 0.88 | |
| 7 | Garcinia cambogia extract Acanthopanax extract | 25 (1:1) | + | 52.34 ± 0.54 | 57.46 ± 0.64 | Extract and compare each |
| | | 50 (1:1) | + | 36.21 ± 0.20 | 76.91 ± 0.25 | |
| 8 | Garcinia cambogia extract Chiisanogenin | 25 (1:1) | + | 61.10 ± 0.54 | 46.90 ± 0.64 | compared to 3 or 5 |
| | | 50 (1:1) | + | 32.36 ± 0.40 | 81.55 ± 0.49 | |
| 9 | Acanthopanax extract Ca-HCA | 25 (1:1) | + | 41.94 ± 0.20 | 70.00 ± 0.24 | compared to 4 or 6 |
| | | 50 (1:1) | + | 36.92 ± 0.20 | 76.05 ± 0.24 | |
| 10 | Ca-HCA Chiisanogenin | 25 (1:1) | + | 46.14 ± 0.54 | 64.94 ± 0.65 | compared to 5 or 6 |
| | | 50 (1:1) | + | 33.53 ± 0.20 | 80.14 ± 0.24 | |

It can be seen that the triglyceride inhibitory effect was higher when *Garcinia cambogia* extract and *Acanthopanax* extract were mixed or when HCA and chiisanogenin were mixed than when *Garcinia* extract, *Acanthopanax* extract, HCA, or Chiisanogenin were administered alone.

Example 7. Confirmation of the Inhibitory Effect of the mRNA Expression of Body Fat Synthesis of the Extract of *Acanthopanax* and *Garcinia cambogia* Extract 3T3-L1 cells, which are preadipocytes of mice, are suspended at a concentration of $2 \times 10^4$ cells/ml using Dulbecco's Modified EaDCRT media (DMEM, Gibco) containing 10% of Bovine Calf Serum as a growth media (GM), and then inoculated into 24-well plates at 1 ml each, and then adipocytes were cultured for 3 days to become confluent. In order to induce adipocyte differentiation, DMEM media containing 10% FBS was replaced with differentiation media (DM) supplemented with insulin, dexamethasone and 3-isobutyl-1-methylanthin (IBMX) and cultured for 2 days. After 2 days, DMEM media containing 10% FBS containing insulin was added to the existing medium. In order to confirm the effect of the drug during the adipocyte differentiation, the drug was treated together when the medium was replaced. After differentiation was induced under the same conditions as above, total RNA was isolated according to the recommended method of TRizol reagent (Ambion). The amount and purity of total RNA was quantified using NanoDrop 2000 (Waltham, MA) and then used in the experiment. cDNA synthesis was performed using Omniscript reverse transcriptase (Qiagen, Valencia, CA) with 1 μg of total RNA and 10 mol oligo-dT18 primer. RT-PCR synthesis was performed according to the recommended experimental method of SYBR Green Master Mix (BioRad and Hercules, Canada). Primers for the genes used in the experiment are shown in Table 10 below. The inhibition rate was calculated according to Math Formula 4 below with the positive control as 100%, and the results are shown in Table 11 below.

In order to determine the statistically significant variance between each group, it was analyzed using a student t-test, and the displayed result value were marked to #$p<0.001$ through comparison with the GM group, and *$p<0.05$, $p<0.01$, and *$p<0.001$ through comparison with the DM group, as statistically significant.

Inhibition rate of body fat synthesis mRNA expression (%) = [Math Formula 3]

$$\left(1 - \frac{\text{(Drug treatment group \%} - \text{Negative Control group \%)}}{\text{(Positive Control group \%} - \text{Negative Control group \%)}}\right) \times 100$$

TABLE 10

| Gene | Forward 5'-3' | Sequence No. | Reverse 5'-3' | Size | Sequence No. |
|---|---|---|---|---|---|
| PPARγ | AGG CCG AGA AGG AGA AGC TGT TG | 1 | TGG CCA CCT CTT TGC TCT GCT C | 276 | 2 |
| C/EBPα | GCA AAG CCA AGA AGT CGG TG | 3 | AGG CGG TCA TTG TCA CTG GT | 139 | 4 |
| FABP4 (aP2) | CAT CAG CGT AAA TGG GGA TT | 5 | TCG ACT TTC CAT CCC ACT TC | 182 | 6 |
| GLUT4 | CTC CTT CTA TTT GCC GTC CTC | 7 | CTG TTT TGC CCC TCA GTC ATT | 194 | 8 |
| FASN | GGC TCT ATG GAT TAC CCA AGC | 9 | CCA GTG TTC GTT CCT CGG A | 190 | 10 |
| β-actin | CAT GTA CGT TGC TAT CCA GG | 11 | CTC CTT AAT GTC ACG CAC GA | 250 | 12 |

TABLE 11

| No | Marker | GM | DM | Garcinia cambogia extract Density (μg/mL) | Chiisanogenin | Body fat synthesis mRNA expression (% relative to β-actin, mean ± deviation) | Inhibition Rate (%, mean ± deviation) |
|---|---|---|---|---|---|---|---|
| 1 | C/EBPα | + | − | 0 | 0 | 7.11 ± 6.88 | — |
| 2 | | − | + | 0 | 0 | 100.00 ± 5.72 # | — |
| 3 | | − | + | 40 | 0 | 94.23 ± 2.07 ** | 6.33 ± 4.06 |
| 4 | | − | + | 30 | 10 | 83.07 ± 1.97 ** | 18.32 ± 4.32 |
| 5 | | − | + | 60 | 20 | 58.27 ± 8.78 *** | 44.99 ± 2.76 |
| 6 | FABP4 | + | − | 0 | 0 | 1.50 ± 2.07 | — |
| 7 | (ap2) | − | + | 0 | 0 | 100.00 ± 2.68 # | — |
| 8 | | − | + | 40 | 0 | 71.58 ± 2.01 ** | 29.01 ± 0.50 |
| 9 | | − | + | 30 | 10 | 63.06 ± 3.56 ** | 37.64 ± 1.13 |
| 10 | | − | + | 60 | 20 | 37.96 ± 3.31 *** | 63.07 ± 1.03 |
| 11 | GLUT4 | + | − | 0 | 0 | 7.32 ± 7.14 | — |
| 12 | | − | + | 0 | 0 | 100.00 ± 2359 # | — |
| 13 | | − | + | 40 | 0 | 71.28 ± 5.59 | 31.23 ± 1.79 |
| 14 | | − | + | 30 | 10 | 60.78 ± 4.67 * | 42.52 ± 0.17 |
| 15 | | − | + | 60 | 20 | 35.39 ± 3.48 *** | 69.82 ± 2.59 |
| 16 | FASN | + | − | 0 | 0 | 1.68 ± 2.07 | — |
| 17 | | − | + | 0 | 0 | 100.00 ± 4.72 # | — |
| 18 | | − | + | 40 | 0 | 91.73 ± 3.88 | 8.71 ± 0.60 |
| 19 | | − | + | 30 | 10 | 61.90 ± 5.73 ** | 38.95 ± 2.33 |
| 20 | | − | + | 60 | 20 | 41.55 ± 1.14 *** | 59.58 ± 1.81 |

Referring to Table 11, compared to the case of using the *Garcinia cambogia* extract (40 ug/mL) alone, the expression of body fat synthesis mRNA was reduced when *Garcinia cambogia* extract and chiisanogenin were used at a mixing ratio of 3:1.

Example 8. Confirmation of the Effect of Suppressing the Expression of Body Fat Synthesis Protein of the Extract of *Acanthopanax* and *Garcinia cambogia* Extract 3T3-L1 cells, which are preadipocytes of mice, are suspended at a concentration of $2 \times 10^4$ cells/ml using Dulbecco's Modified EaDCRT media (DMEM, Gibco) containing 10% of Bovine Calf Serum as a growth media (GM), and then inoculated into 24-well plates at 1 ml each, and then adipocytes were cultured for 3 days to become confluent. In order to induce adipocyte differentiation, DMEM media containing 10% FBS was replaced with differentiation media (DM) supplemented with insulin, dexamethasone and 3-isobutyl-1-methylxanthin (IBMX) and cultured for 2 days. After 2 days, DMEM media containing 10% FBS containing insulin was added to the existing medium. In order to confirm the effect of the drug during the adipocyte differentiation, the drug was treated together when the medium was replaced. After differentiation was induced under the same conditions as above, cells were collected with a scraper after culture and washed with phosphate buffered saline (Hyclone, SH30258.01). Cells were homogenized after adding protease inhibitor cocktail tablets to RIPA buffer (Elpis Biotech, Daejeon, South Korea), which is a protein extraction solution. After reacting on ice for 30 minutes and centrifuging at 13000 rpm, 4° C. for 15 minutes, the supernatant was transferred to a new tube. After quantification of the protein by the BCA method using a BCA protein assay kit (Thermo, 23227), samples were made at a constant concentration. After loading on an SDS-PAGE gel, electrophoresis was performed at 100 V for 120 minutes. After the gel was transferred to a PDVF membrane activated in 100% methanol at 400 mA for 60 minutes, 5× protein-free General block solution (Translab, TLP-115.1 G) and DW were used to make 1× blocking solution and block for 60 minutes. A primary antibody for the protein to be identified was added and reacted at 4° C. for 16 hours. After washing with PBS-T, a secondary antibody was added and reacted for 60 minutes, followed by washing with PBS-T. Bands were detected using ECL solution (Thermo, 34580). Protein bands were detected by Amersham Imager 680 and visualized using Amersham Imager 680 Analysis Software (Version 2.0.0).

a-tubulin was used as an intracellular protein loading control. The results are shown in FIG. 5.

Figure 5:
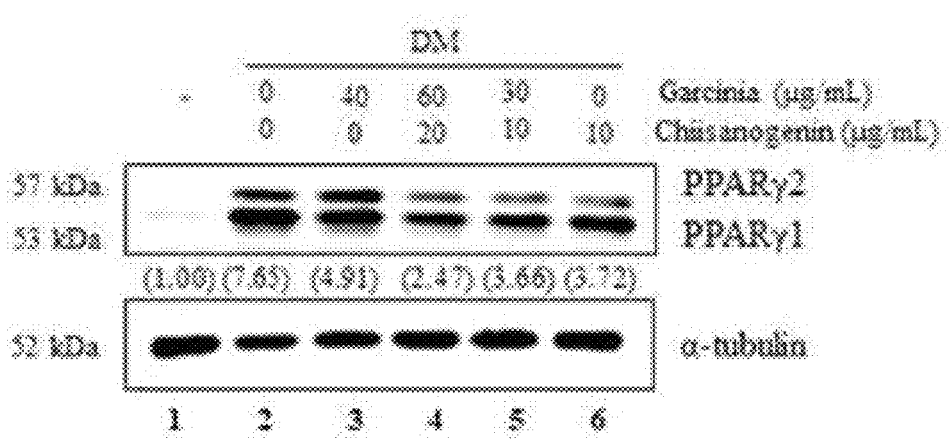
FIG. 5 is a graph showing the amount of PPARγ expression according to the treatment of a negative control, a *Garcinia cambogia* extract positive control, an *Acanthopanax* extract positive control, and a mixture of *Garcinia cambogia* extract and *Acanthopanax* extract.

Referring to FIG. 5, as a result of confirming the expression level of PPARγ, a transcription factor that regulates obesity-related genes, by western blot, the inhibitory effect was increased when *Garcinia cambogia* extract (30 μg/mL) was treated with chiisanogenin (10 μg/mL) or *Garcinia cambogia* extract (60 μg/mL) was treated with chiisanogenin (20 μg/mL) compared to the treatment with *Garcinia* extract (40 μg/mL) or chiisanogenin (10 μg/mL) alone.

Example 9. Confirmation of the Effects of *Garcinia cambogia* Extract and *Acanthopanax* Extract on Promoting Glucose Uptake in Muscle Cells To differentiate rat myoblast L6 cells into myotubes, it was suspended at a concentration of $1 \times 10^4$ cells/ml in MEM medium (Welgene) supplemented with 10% of Fetal Bovine Serum and 1% of antibiotic antimycotic, and then 500 μl each was inoculated into a 24-well plate and cultured to the full for 2 days. Thereafter, the medium was cultured for 7 days while replacing the medium once every 2 days with MEM medium containing 2% bovine serum. The differentiated myotube cells were replaced with serum-free medium before the experiment and left for 6 hours. Myotube cells were pretreated with 100 nM porcine-derived insulin and 20 μM cytochalacin B for 15 minutes, and other samples were pretreated for 30 minutes. Thereafter, 0.2 μCi/mL 2-deoxy-D-[14 C]-glucose (2-DG) was treated and incubated at 37° C. for 5 minutes. After the reaction, the cells were washed twice with Krebs-Ringer buffer (20 mM Tris-HCl, 2 mM EDTA, and 0.5 mM EGTA, pH 7.4), and the cells were lysed with 0.5N NaOH and mixed with a scintillation cocktail. The intracellular radiation dose of 2-DG was measured using a liquid scintillation counter (Tri-Carb 2900TR liquid scintillation analyzer, Perkin Elmer).

The intracellular glucose uptake rate was calculated according to Math Formula 5 below, and then the calculated value was corrected using GraphPad Prism as 0% for the control group and 100% for the insulin-treated group. The results are shown in Table 12 below.

[Math Formula 5]
$$\text{Glucose Uptake Rate (\%)} = \frac{(DPM_{Sample\ treatment\ group} - DPM_{cytochalacinB})}{(DPM_{Control\ group} - DPM_{cytochalacinB})} \times 100$$

TABLE 12

| No. | | Density (μg/mL) | | | Glucose absorption rate (%, relative conversion value based on the glucose absorption rate by 100 nM insulin treatment as 100%) | ±Standard deviation |
|---|---|---|---|---|---|---|
| | | A + B | A | B | | |
| 1 | A: Garcinia cambogia | 50 | 50 | 0 | 8 | 3.713 |
| 2 | extract + B: | | 0 | 50 | 28 | 3.643 |
| 3 | Acanthopanax extract | | 25 | 25 | 13 | 2.431 |
| 4 | | 100 | 100 | 0 | 23 | 5.621 |
| 5 | | | 0 | 100 | 42 | 3.977 |
| 6 | | | 50 | 50 | 42 | 0.928 |
| 7 | | 150 | 150 | 0 | 51 | 1.813 |
| 8 | | | 0 | 150 | 51 | 9.559 |
| 9 | | | 75 | 75 | 62 | 1.857 |

TABLE 12-continued

| No. | | Density (μg/mL) | | | Glucose absorption rate (%, relative conversion value based on the glucose absorption rate by 100 nM insulin treatment as 100%) | ±Standard deviation |
|---|---|---|---|---|---|---|
| | | A + C | A | C | | |
| 10 | A: Garcinia cambogia | 100 | 100 | 0 | 23 | 5.621 |
| 11 | extract + C: | | 0 | 10 | 14 | 6.060 |
| 12 | Chiisanogenin | | 90 | 10 | 40 | 7.930 |
| 13 | | 150 | 150 | 0 | 48 | 1.260 |
| 14 | | | 0 | 15 | 25 | 0.998 |
| 15 | | | 135 | 15 | 76 | 3.098 |
| 16 | | 200 | 200 | 0 | 54 | 2.678 |
| 17 | | | 0 | 20 | 41 | 3.249 |
| 18 | | | 180 | 20 | 107 | 0.788 |
| | | B + D | B | D | | |
| 19 | B: Acanthopanax | 50 | 50 | 0 | 28 | 3.643 |
| 20 | extract + D: Ca-HCA | | 0 | 10 | 18 | 3.686 |
| 21 | | | 40 | 10 | 43 | 0.947 |
| 22 | | 100 | 100 | 0 | 42 | 3.977 |
| 23 | | | 0 | 20 | 44 | 5.333 |
| 24 | | | 80 | 20 | 79 | 0.105 |
| 25 | | 150 | 150 | 0 | 51 | 9.559 |
| 26 | | | 0 | 30 | 50 | 6.211 |
| 27 | | | 120 | 30 | 94 | 4.947 |
| | | C + D | C | D | | |
| 28 | C: Chiisanogenin + | 5 | 5 | 0 | 1 | 4.159 |
| 29 | D: Ca-HCA | | 0 | 5 | 5 | 0.192 |
| 30 | | | 2.5 | 2.5 | 5 | 0.768 |
| 31 | | 10 | 10 | 0 | 18 | 3.686 |
| 32 | | | 0 | 10 | 14 | 6.060 |
| 33 | | | 5 | 5 | 34 | 1.792 |
| 34 | | 20 | 20 | 0 | 44 | 5.333 |
| 35 | | | 0 | 20 | 41 | 3.249 |
| 36 | | | 10 | 10 | 97 | 10.687 |

It means that muscle cells have a high glucose uptake rate to lower the increased blood sugar level. Referring to Table 12, it can be seen that glucose uptake into muscle cells is higher in the case of using the mixture of the *Acanthopanax* extract and *Garcinia cambogia* extract, or in the case of using the mixture of HCA and chiisanogenin than in the case of using the *Acanthopanax* extract, *Garcinia cambogia* extract, HCA or chiisanogenin alone.

Example 10. Anti-Diabetic Synergistic Effect Verification by Combined Treatment with Chiisanogenin and Ca-HCA Compound Isobologram analysis was used to confirm the synergistic effect of the combination of chiisanogenin and HCA. The glucose absorption capacity of the differentiated L6 myotube cells was measured in the same manner as in Example 9, and the $EC_{50}$ of chiisanogenin was 23.32 μM and the $EC_{50}$ of Ca-HCA was 27.6 μM. Next, the $EC_{50}$ value of Ca-HCA was calculated by fixing a concentration of 12 μM corresponding to ½ of the $EC_{50}$ value of chiisanogenin and combining with Ca-HCA in various concentration ranges. Conversely, the $EC_{50}$ value of chiisanogenin was calculated by fixing a concentration of 14 μM corresponding to ½ of the Ca-HCA $EC_{50}$ value and combining with chiisanogenin in various concentration ranges. The CI value was calculated by substituting each value into Math Formula 6 below, and the two compounds were judged to be antagonistic if CI>1, additive if CI=1, and synergistic if CI<1.

[Math Formula 6]

$$\text{Combination index }(CI) = \frac{C_{chiisanogenin}}{EC_{50\,chiisanogenin}} + \frac{C_{Ca-HCA}}{EC_{50\,Ca-HCA}}$$

Figure 6:
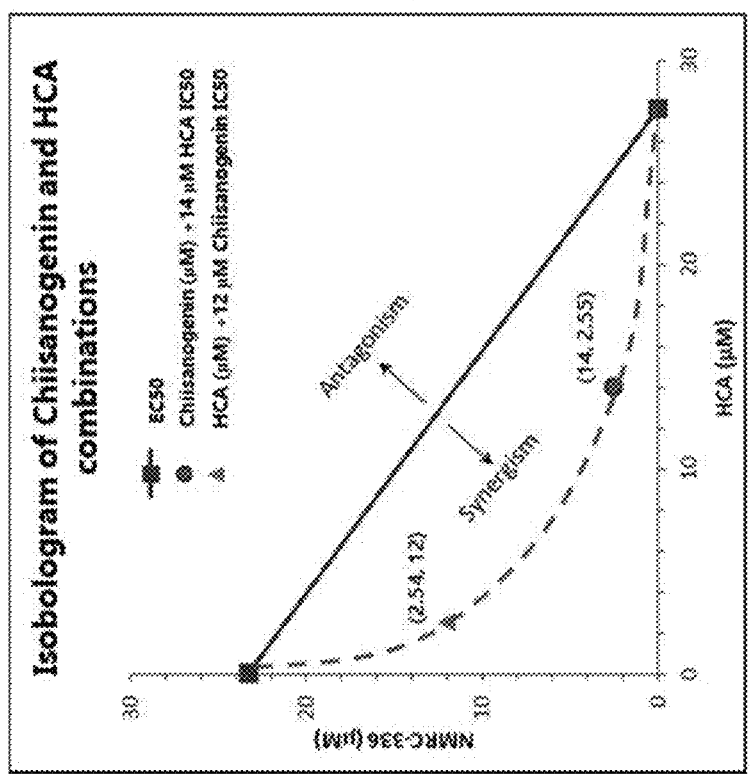
FIG. 6 is a graph showing the anti-diabetic synergistic effect according to the combined use of HCA and chiisanogenin.

The CI value was calculated accordingly and is shown in FIG. 6.

The calculation results are shown in FIG. 6.

Example 11. Verification of Synergistic Effect in Vivo by Combined Treatment of *Acanthopanax* Extract and *Garcinia cambogia* Extract After adapting 8-week-old male C57bl/6 J mice to the basic diet (AIN-76A diet) for 2 weeks, and consuming Diet Induced Obesity Diet Formulas (D12451) 60 kcal % HFD diet for 2 weeks from 10 weeks of age, and then the test drug was administered when the average body weight reached 28 g or more. The animal breeding room environment of the mouse was maintained in a constant temperature (25±2° C.), constant humidity (50±5%) and a 12-hour photoperiod (light on 07:00~19:00) in which the light and shade were controlled in an SPF environment. The experimental group was set as a single sample (*Garcinia cambogia* extract, *Acanthopanax* extract), a composite sample thereof (*Garcinia cambogia* extract+*Acanthopanax* extract), and a positive control group (Metformin), and 10 animals per group were administered in parallel with the HFD diet once daily for 10 weeks. The test drug was dispersed in 0.5% Carboxymethyl cellulose (CMC) and administered in a volume of 0.2 ml, and the drug was administered orally by force into the stomach using a metal Zonde for oral administration.

11-1. Weight Change, Dietary Efficiency and Organ Weight Change

Body weight and food intake were measured and recorded at regular times every week.

Total weight gain: weight at the end of the experiment−weight at the start of the experiment (1)

Food intake=average food intake per day−total feed intake/days (2)

Food efficiency ratio (FER)=[total weight gain/total food intake]×100 (3)

As shown in Table 13 below, it was confirmed that a significant decrease in dietary efficiency was observed in the combined treatment group of the *Acanthopanax* extract and *Garcinia cambogia* extract compared to the group treated with each extract alone. A decrease in dietary efficiency can help reduce body fat.

In addition, no change in the weight of the kidney and spleen means that the test substance is not toxic to organs related to metabolism and immunity.

TABLE 13

| No | Marker | HFD | Acanthopanax extract Density (mg/kg) | Garcinia cambogia extract | mean ± standard error | Inhibition Rate (%) |
|---|---|---|---|---|---|---|
| 1 | Final | − | — | — | 31.2 ± 0.91 | |
| 2 | weight (g) | + | — | — | 44.3 ± 0.92 ### | |
| 3 | | + | 200 | — | 38.6 ± 1.06 *** | 43 |
| 4 | | + | — | 200 | 37.6 ± 1.18 *** | 51 |
| 5 | | + | 100 | 100 | 38.7 ± 1.21 ** | 43 |
| 6 | | + | Met 50 mg/kg | | 38.6 ± 0.93 *** | 43 |
| 7 | Weight | − | — | — | 9.2 ± 0.67 | |
| 8 | gain (g) | + | — | — | 21.6 ± 0.80 ### | |
| 9 | | + | 200 | — | 14.6 ± 1.07 *** | 57 |
| 10 | | + | — | 200 | 14.4 ± 1.18 *** | 58 |
| 11 | | + | 100 | 100 | 14.3 ± 0.72 *** | 59 |
| 12 | | + | Met 50 mg/kg | | 15.3 ± 0.82 *** | 51 |
| 13 | Food | + | — | — | 3.06 | |
| 14 | intakes | + | — | — | 2.29 | |
| 15 | (g/day):Food | − | 200 | — | 2.27 | |
| 16 | intake | + | — | 200 | 2.39 | |
| 17 | | + | 100 | 100 | 2.36 | |
| 18 | | + | Met 50 mg/kg | | 2.24 | |
| 19 | FER (%):Food | − | — | — | 4.3 ± 0.31 | |
| 20 | efficiency | + | — | — | 13.5 ± 0.50 ### | |
| 21 | ratio | + | 200 | — | 9.2 ± 0.68 *** | 47 |
| 22 | | + | — | 200 | 8.6 ± 0.70 *** | 53 |
| 23 | | + | 100 | 100 | 8.0 ± 0.51 *** | 60 |
| 24 | | + | Met 50 mg/kg | | 9.7 ± 0.52 *** | 41 |
| 25 | Kidney (g) | − | — | — | 0.25 ± 0.02 | |
| 26 | | + | — | — | 0.23 ± 0.02 | |
| 27 | | + | 200 | — | 0.23 ± 0.02 | |
| 28 | | + | — | 200 | 0.23 ± 0.02 | |
| 29 | | + | 100 | 100 | 0.24 ± 0.02 | |
| 30 | | + | Met 50 mg/kg | | 0.31 ± 0.01 | |
| 31 | Spleen (g) | − | — | — | 0.10 ± 0.00 | |
| 32 | | + | — | — | 0.10 ± 0.00 | |
| 33 | | + | 200 | — | 0.10 ± 0.00 | |
| 34 | | + | — | 200 | 0.10 ± 0.00 | |
| 35 | | + | 100 | 100 | 0.10 ± 0.00 | |
| 36 | | + | Met 50 mg/kg | | 0.10 ± 0.00 | |

11-2. Body Fat Reduction

After removing retroperitoneal white adipose tissue and intestines white adipose tissue of each experimental animal, the weight of adipose tissue was calculated.

As shown in Table 14 below, it was confirmed that the reduction rate of white fat in the body was greatly improved in the combined treatment group of the *Acanthopanax* extract and *Garcinia cambogia* extract compared to the group treated with each extract alone.

TABLE 14

| No | Marker | HFD | Acanthopanax extract Density (mg/kg) | Garcinia cambogia extract | mean ± standard error | Inhibition Rate (%) |
|---|---|---|---|---|---|---|
| 1 | Retroperitoneal | − | — | — | 0.18 ± 0.02 | |
| 2 | white adipose | + | — | — | 1.00 ± 0.06 ### | |

TABLE 14-continued

| No | Marker | HFD | Acanthopanax extract Density (mg/kg) | Garcinia cambogia extract | mean ± standard error | Inhibition Rate (%) |
|---|---|---|---|---|---|---|
| 3 | tissue (g) | + | 200 | — | 0.88 ± 0.07 | 14 |
| 4 | | + | — | 200 | 0.84 ± 0.07 | 17 |
| 5 | | + | 100 | 100 | 0.83 ± 0.04 | 19 |
| 6 | | + | Met 50 mg/kg | | 0.89 ± 0.06 | 12 |
| 7 | Intestines WAT | − | — | — | 0.13 ± 0.02 | |
| 8 | (g) | + | — | — | 0.91 ± 0.05 ### | |
| 9 | | + | 200 | — | 0.43 ± 0.05 *** | 51 |
| 10 | | + | — | 200 | 0.51 ± 0.06 *** | 51 |
| 11 | | + | 100 | 100 | 0.62 ± 0.07 ** | 53 |
| 12 | | + | Met 50 mg/kg | | 0.55 ± 0.05 *** | 46 |

11-3. Oral Glucose Tolerance Test

After administering the test drug for 10 weeks, the mice were fasted for 12 hours one day before necropsy, and blood glucose was measured, and glucose (1 g/kg) was intraperitoneally administered (i.p) immediately, and blood glucose was measured at 0 and 30 minutes. Blood to be used for blood glucose measurement was collected from the tail vein of a mouse, and blood glucose was measured using a serum analyzer (Accutrend plus GCTL Cobas Roche, Germany).

As shown in Table 15 below, it was confirmed that the Oral glucose tolerance inhibition rate was significantly higher in the group treated with the combined treatment of the *Acanthopanax* extract and *Garcinia cambogia* extract compared to the group treated with each extract alone.

TABLE 15

| No | Marker | HFD | Acanthopanax extract Density (mg/kg) | Garcinia cambogia extract | mean ± standard error | Inhibition Rate (%) |
|---|---|---|---|---|---|---|
| 1 | OGTT | − | — | — | 45 ± 10.50 | |
| 2 | (30 min- | + | — | — | 179 ± 15.12 ### | 32 |
| 3 | 0 min, | + | 200 | — | 135 ± 9.13 | 32 |
| 4 | mg/dL) | + | — | 200 | 126 ± 11.53 * | 39 |
| 5 | | + | 100 | 100 | 118 ± 15.99 * | 45 |
| 6 | | + | Met 50 mg/kg | | 148 ± 18.50 | 23 |

11-4. Serum Test

Blood was collected by cardiac puncture to conduct a blood biochemical test after the end of the final experiment, and then plasma was separated by centrifugation at 3,000 rpm and 4° C. for 15 minutes within 30 minutes after blood collection, and then stored at −74° C. for blood chemistry and ELISA analysis. The contents of total cholesterol, high-density lipoprotein (HDL), low-density lipoprotein (LDL), triglyceride, FFA, glucose, and LDH, which are indicators of lipid content, were measured using an automated biochemical analyzer (Hitachi-720, Hitachi Medical, Japan). IGF-1 and Creatine were diluted in coating buffer, coated on microwells, and left overnight at 4° C. After washing each well with the buffer solution three times, 100 μl of serum (10-fold dilution) was dispensed, left at room temperature for 1 hour, and then washed twice with the buffer solution. Thereafter, 100 μl of the antibody avidin-HRP conjugate was treated, left at room temperature for 1 hour, and then washed again. 100 μl of the TMB substrate was dispensed, left in the dark for 30 minutes, treated with 50 μl of the stop solution, and absorbance was measured at a wavelength of 450 nm using an ELISA reader.

As shown in Table 16 below, it was confirmed that the IGF-1 inhibition rate was remarkably high in the combined treatment group of the *Acanthopanax* extract and *Garcinia cambogia* extract compared to the group treated with each extract alone. Since an increase in IGF-1 is related to an increase in leptin, and an increase in body fat increases blood leptin, significant inhibition of IGF-1 expression means that body fat is reduced.

In addition, it was confirmed that the creatine inhibition rate was remarkably superior in the combined treatment group of the *Acanthopanax* extract and *Garcinia cambogia* extract compared to the group treated with each extract alone. Since increased creatine is associated with an increased risk of metabolic syndrome, including cardiovascular disease, obesity, and hypertension (Korean J clin Lab Sci 2019; 51:42-49), it can be interpreted that the preventive or therapeutic effects such as obesity of the combined treatment group are significantly superior to those of each single treatment group.

TABLE 16

| No | Marker | HFD | Acanthopanax extract Density (mg/kg) | Garcinia cambogia extract | mean ± standard error | Inhibition Rate (%) |
|---|---|---|---|---|---|---|
| 1 | IGF-1 | − | — | — | 1147.6 ± 58.24 | |
| 2 | (pg/ml) | + | — | — | 3831.4 ± 136.45 ### | |
| 3 | | + | 200 | — | 3309.7 ± 65.77 ** | 19 |
| 4 | | + | — | 200 | 2650.9 ± 140.14 *** | 44 |
| 5 | | + | 100 | 100 | 1815.4 ± 139.65 *** | 75 |
| 6 | | + | Met 50 mg/kg | | 1455.8 ± 138.07 *** | 89 |
| 7 | Creatin | − | — | — | 0.603 ± 0.014 | |
| 8 | (mg/dL) | + | — | — | 0.656 ± 0.008 ### | |
| 9 | | + | 200 | — | 0.610 ± 0.017 * | 87 |
| 10 | | + | — | 200 | 0.611 ± 0.012 ** | 86 |
| 11 | | + | 100 | 100 | 0.605 ± 0.008 ** | 96 |
| 12 | | + | Met 50 mg/kg | | 0.564 ± 0.011 *** | 175 |
| 13 | Glucose | − | — | — | 83.1 ± 9.14 | |
| 14 | (mg/dL) | + | — | — | 217.3 ± 12.02 ### | |
| 15 | | + | 200 | — | 181.9 ± 15.55 | 26 |
| 16 | | + | — | 200 | 188.5 ± 19.06 | 21 |
| 17 | | + | 100 | 100 | 168.0 ± 10.82 * | 37 |
| 18 | | + | Met 50 mg/kg | | 202.5 ± 7.98 | 11 |
| 19 | Cholesterol | − | — | — | 121.1 ± 5.48 | |
| 20 | (mg/dL) | + | — | — | 212.2 ± 10.70 ### | |
| 21 | | + | 200 | — | 186.0 ± 6.48 | 29 |
| 22 | | + | — | 200 | 192.3 ± 11.21 | 22 |
| 23 | | + | 100 | 100 | 180.6 ± 4.07 * | 35 |
| 24 | | + | Met 50 mg/kg | | 175.6 ± 9.03 | 40 |
| 25 | Triglyceride | − | — | — | 100.2 ± 12.27 | |
| 26 | (mg/dL) | + | — | — | 153.4 ± 5.69 ### | |
| 27 | | + | 200 | — | 106.0 ± 4.48 *** | 89 |
| 28 | | + | — | 200 | 106.8 ± 4.25 *** | 88 |
| 29 | | + | 100 | 100 | 96.3 ± 3.19 *** | 107 |
| 30 | | + | Met 50 mg/kg | | 118.6 ± 5.90 *** | 65 |
| 31 | HDL | − | — | — | 71.2 ± 3.03 | |
| 32 | (mg/dL) | + | — | — | 89.3 ± 2.90 ### | |
| 33 | | + | 200 | — | 87.8 ± 2.11 | 9 |
| 34 | | + | — | 200 | 88.1 ± 1.92 | 6 |
| 35 | | + | 100 | 100 | 84.6 ± 1.28 | 26 |
| 36 | | + | Met 50 mg/kg | | 88.1 ± 2.99 | 7 |
| 37 | LDL | − | — | — | 10.2 ± 0.63 | |
| 38 | (mg/dL) | + | — | — | 17.4 ± 1.10 ### | |
| 39 | | + | 200 | — | 13.7 ± 0.21 * | 52 |
| 40 | | + | — | 200 | 13.8 ± 1.01 * | 50 |
| 41 | | + | 100 | 100 | 13.6 ± 0.68 * | 53 |
| 42 | | + | Met 50 mg/kg | | 12.3 ± 0.80 ** | 71 |
| 43 | LDH | − | — | — | 714.9 ± 91.24 | |
| 44 | (U/L) | + | — | — | 1265.4 ± 70.88 ### | |
| 45 | | + | 200 | — | 639.5 ± 35.95 *** | 114 |
| 46 | | + | — | 200 | 590.0 ± 41.30 *** | 123 |
| 47 | | + | 100 | 100 | 496.6 ± 36.33 *** | 140 |
| 48 | | + | Met 50 mg/kg | | 592.0 ± 53.77 *** | 122 |
| 49 | NEFA | − | — | — | 1.87 ± 0.10 | |
| 50 | (mEq/L) | + | — | — | 2.88 ± 0.09 ### | |
| 51 | | + | 200 | — | 2.41 ± 0.10 ** | 47 |
| 52 | | + | — | 200 | 2.28 ± 0.22 * | 60 |
| 53 | | + | 100 | 100 | 2.21 ± 0.13 *** | 66 |
| 54 | | + | Met 50 mg/kg | | 2.26 ± 0.10 *** | 61 |

11-5. Adipose Tissue C/EBP-α mRNA Analysis

RNA was extracted from tissues using RNAsolB (Tel-Test) solution, and cDNA and real-time PCR analysis were performed using One-step SYBR Green PCR kit (AB science). Add 500 μl of RNAzolB to the adipose tissue, pulverize the tissue with a homogenizer, add 50 μl of chloroform, and mix again for 15 seconds. After being left on ice for 15 minutes, centrifuged at 13,000 rpm, about 200 μl of the supernatant was collected, mixed with 200 μl of 2-propanol in the same amount, shaken slowly, and left on ice for 15 minutes. RNA was extracted by centrifuging again at 13,000 rpm, washing with 80% EtOH, and drying with a vacuum pump for 3 minutes. The extracted RNA was dissolved in 20 μl of diethyl pyrocarbonate (DEPC)-treated distilled water, inactivated in a heating block at 75° C., and used for first strand cDNA synthesis. For the reverse transcription reaction, 3 μg of the prepared total RNA was reacted with 2 U/tube of DNase I (10 U/μl) at 37° C. lock for 30 minutes, then denatured at 75° C. for 10 minutes, 2.5 μl of 10 mM dNTPs mix, 1 μl random sequence hexanucleotides (25 pmoles/25 μl), 1 μl RNase inhibitor (20 U/μl) as RNA inhibitor, 1 μl 100 mM DTT, 4.5 μl 5× RT buffer (250 mM Tris-HCl, pH 8.3, 375 mM KCl, 15 mM MgCl2) was added thereto, and 1 μl of M-MLU RT (200 U/μl) was added again and the final volume was 20 μl with DEPC treated distilled water. After mixing well, 20 μl of the reaction mixture was centrifuged at 2,000 rpm for 5 seconds and reacted at 37° C. lock for 45 minutes to synthesize first-strand cDNA and then left at 95° C. for 5 minutes to inactivate M-MLV RT, the synthesized cDNA is used for polymerase chain reaction (PCR). A forward 5'-TGGACAAGAACAGCAACGAGTAC-3' (SEQ ID NO:

13) and a reverse 5'-CGGTCATTGTCACTGGTCAACT-3' (SEQ ID NO: 14) was used to amplify C/EBP-α mRNA and a VIC probe of 5'-TGCATCCTGCACCACCAACTGCT-TAG-3' (SEQ ID NO: 15) sequence was used to amplify GAPDH mRNA as an intra control. Real time quantitative PCR was performed using the Applied Biosystems 7500 Real-Time PCR system (Applied Biosystems, USA).

As shown in Table 17 below, it was confirmed that the inhibition rate of C/EBP-α mRNA expression in adipose tissue was significantly higher in the group treated with the combination of the *Acanthopanax* extract *Garcinia cambogia* extract compared to the group treated with each extract alone. Since C/EBP-α is a transcription factor involved in adipocyte differentiation, the excellent effect of suppressing its expression means that it can help reduce body fat.

TABLE 17

| No | Marker | HFD | Acanthopanax extract Density (mg/kg) | Garcinia cambogia extract | mean ± standard error | Inhibition Rate (%) |
|---|---|---|---|---|---|---|
| 1 | C/EBP-α | − | — | — | 0.563 ± 0.137 | |
| 2 | | + | — | — | 2.951 ± 0.591 ## | |
| 3 | | + | 200 | — | 2.405 ± 0.252 * | 23 |
| 4 | | + | — | 200 | 1.882 ± 0.424 | 45 |
| 5 | | + | 100 | 100 | 1.011 ± 0.304 * | 81 |
| 6 | | + | Met 50 mg/kg | | 1.153 ± 0.320 * | 75 |

11-6. Statistical Processing

Results obtained from various experiments are recorded as mean±standard error of mean (SEM), and significance verification is determined using the student's T-test analysis method. The data were analyzed using one-way ANOVA to determine a statistically significant variance between each group for each final point measured, and statistical significance between each group was determined using the non-parametric Mann-Whitney test and Dunnett's multiple comparison test (IBM SPSS statistics version 19.0 statistic software, Inc, IBM, USA). The displayed result values were marked to ##p<0.01, ###p<0.001 through comparison with the normal control group, and *p<0.05, p<0.01, *p<0.001 through comparison with the HFD group as statistically significant of the criterion.

Example 12. In Vivo Verification of Synergistic Effect by Combined Treatment of Chiisanogenin and *Garcinia cambogia* Extract After adapting 8-week-old male C57b1/6 J mice to the basic diet (AIN-76A diet) for 2 weeks, and consuming Diet Induced Obesity Diet Formulas (D12451) 60 kcal % HFD diet for 2 weeks from 10 weeks of age, and then the test drug was administered when the average body weight reached 28 g or more. The animal breeding room environment of the mouse was maintained in a constant temperature (25±2° C.), constant humidity (50±5%) and a 12-hour photoperiod (light on 07:00~19:00) in which the light and shade were controlled in an SPF environment. The experimental group was set as a single sample (*Garcinia cambogia* extract or chiisanogenin), a composite sample thereof (*Garcinia cambogia* extract+chiisanogenin), and a positive control group (Metformin), and 10 animals per group were administered in parallel with the HFD diet once daily for 10 weeks. The test drug was dispersed in 0.5% Carboxymethyl cellulose (CMC) and administered in a volume of 0.2 ml, and the drug was administered orally by force into the stomach using a metal Zonde for oral administration.

12-1. Oral Glucose Tolerance Test

After administering the test drug for 10 weeks, the mice were fasted for 12 hours one day before necropsy, and blood glucose was measured, and glucose (1 g/kg) was intraperitoneally administered (i.p) immediately, and blood glucose was measured at 0 and 30 minutes. Blood to be used for blood glucose measurement was collected from the tail vein of a mouse, and blood glucose was measured using a serum analyzer (Accutrend plus GCTL Cobas Roche, Germany).

As shown in Table 18 below, it was confirmed that the Oral glucose tolerance inhibition rate was significantly higher in the group treated with the combined treatment of chiisanogenin and *Garcinia cambogia* extract compared to the group treated with each extract alone.

TABLE 18

| No | Marker | HFD | Chiisanogenin Density (mg/kg) | Garcinia cambogia extract | mean ± standard error | Inhibition Rate (%) |
|---|---|---|---|---|---|---|
| 1 | OGTT | − | — | — | 45.0 ± 10.50 | |
| 2 | (30 min- | + | — | — | 178.6 ± 15.12 ### | |
| 3 | 0 min, | + | 50 | — | 127.4 ± 13.03 * | 38 |
| 4 | mg/dL) | + | — | 200 | 126.0 ± 11.53 | 39 |
| 5 | | + | 50 | 150 | 120.3 ± 19.36 * | 44 |
| 6 | | + | Met 50 mg/kg | | 148.0 ± 18.50 | 23 |

12-2. Serum Test

Blood was collected by cardiac puncture to conduct a blood biochemical test after the end of the final experiment, and then plasma was separated by centrifugation at 3,000 rpm and 4° C. for 15 minutes within 30 minutes after blood collection, and then stored at −74° C. for blood chemistry and ELISA analysis. The contents of total cholesterol, high-density lipoprotein (HDL), low-density lipoprotein (LDL), triglyceride, FFA, glucose, and LDH, which are indicators of lipid content, were measured using an automated biochemical analyzer (Hitachi-720, Hitachi Medical, Japan). IGF-1 and Creatine were diluted in coating buffer, coated on microwells, and left overnight at 4° C. After washing each well with the buffer solution three times, 100 µl of serum (10-fold dilution) was dispensed, left at room temperature for 1 hour, and then washed twice with the buffer solution. Thereafter, 100 µl of the antibody avidin-HRP conjugate was treated, left at room temperature for 1 hour, and then washed again. 100 µl of the TMB substrate was dispensed, left in the dark for 30 minutes, treated with 50 µl of the stop solution, and absorbance was measured at a wavelength of 450 nm using an ELISA reader.

As shown in Table 19 below, it was confirmed that the creatine inhibition rate was remarkably high in the combined treatment group of chiisanogenin and *Garcinia cambogia* extract compared to the group treated with each extract alone. Since increased creatine is associated with an increased risk of metabolic syndrome, including cardiovascular disease, obesity, and hypertension (Korean J din Lab Sci 2019; 51:42-49), it can be interpreted that the preventive or therapeutic effects such as obesity of the combined treatment group are significantly superior to those of each single treatment group.

TABLE 19

| No | Marker | HFD | Chiisanogenin Density (mg/kg) | Garcinia cambogia extract | mean ± standard error | Inhibition Rate (%) |
|---|---|---|---|---|---|---|
| 1 | Creatin | − | — | — | 0.603 ± 0.014 | |
| 2 | (mg/dL) | + | — | — | 0.656 ± 0.008 ### | |
| 3 | | + | 50 | — | 0.635 ± 0.007 * | 87 |
| 4 | | + | — | 200 | 0.611 ± 0.012 ** | 86 |
| 5 | | + | 50 | 150 | 0.606 ± 0.016 ** | 96 |
| 6 | | + | Met 50 mg/kg | | 0.564 ± 0.011 *** | 175 |

12-3. Adipose Tissue PPAR-Gamma mRNA Analysis

RNA was extracted from tissues using RNAsolB (Tel-Test) solution, and cDNA and real-time PCR analysis were performed using One-step SYBR Green PCR kit (AB science).

From the prepared cDNA, a FAM probe of 5'-TCGGAATCAGCTCTGTGGACCTCTCC-3' (SEQ ID NO: 16) sequence was used to amplify PPAR-gamma mRNA, and a VIC probe of 5'-TGCATCCTGCACCACCAACTGCTTAG-3' (SEQ ID NO: 15) sequence was used to amplify GAPDH mRNA as an intra control. Real time quantitative PCR was performed using the Applied Biosystems 7500 Real-Time PCR system (Applied Biosystems, USA).

As shown in Table 20 below, it was confirmed that the inhibition rate of PPAR-gamma mRNA expression was remarkably improved in the combined treatment group of chiisanogenin and *Garcinia cambogia* extract compared to each treatment alone.

TABLE 20

| No | Marker | HFD | Chiisanogenin Density (mg/kg) | Garcinia cambogia extract | mean ± standard error | Inhibition Rate (%) |
|---|---|---|---|---|---|---|
| 1 | PPAR-γ | − | — | — | 0.671 ± 0.21 | |
| 2 | | + | — | — | 3.526 ± 0.73 ## | |
| 3 | | + | 50 | — | 2.134 ± 0.39 * | 49 |
| 4 | | + | — | 200 | 2.465 ± 0.64 | 37 |
| 5 | | + | 50 | 150 | 1.944 ± 0.26 * | 55 |
| 6 | | + | Met 50 mg/kg | | 1.235 ± 0.42 * | 80 |

12-4. Statistical Processing

Results obtained from various experiments are recorded as mean±standard error of mean (SEM), and significance verification is determined using the student's T-test analysis method. The data were analyzed using one-way ANOVA to determine a statistically significant variance between each group for each final point measured, and statistical significance between each group was determined using the non-parametric Mann-Whitney test and Dunnett's multiple comparison test (IBM SPSS statistics version 19.0 statistic software, Inc, IBM, USA). The displayed result values was marked to ##p<0.01, ###p<0.001 through comparison with the normal control group, and *p<0.05, p<0.01, *p<0.001 through comparison with the HFD group as statistically significant of the criterion.

What is claimed is:

1. A pharmaceutical composition for treating diabetes or obesity, comprising a first component of *Acanthopanax* extract, chiisanogenin, or chiisanogenin derivative, and a second component of *Garcinia cambogia* extract or hydroxy citric acid (HCA).

2. The composition according to claim 1, wherein the first component and the second component are included in a weight ratio of 5:1 to 1:20.

3. The composition according to claim 1, wherein the first component is chiisanogenin, and the second component is *Garcinia cambogia* extract.

4. The composition according to claim 3, wherein the first component and the second component are included in a weight ratio of 1:1 to 1:9.

5. The composition according to claim 1, wherein the first component is *Acanthopanax* extract, and the second component is HCA.

6. The composition according to claim 5, wherein the first component and the second component are included in a weight ratio of 5:1 to 1:1.

7. A method of treating diabetes or obesity comprising administering an effective amount of the composition according to claim 1 to a subject in need thereof.

8. The method according to claim 7, wherein the first component and the second component are included in a weight ratio of 5:1 to 1:20.

9. The method according to claim 7, wherein the first component is chiisanogenin, and the second component is *Garcinia cambogia* extract.

10. The method according to claim 7, wherein the first component is *Acanthopanax* extract, and the second component is HCA.

* * * * *

```
                        SEQUENCE LISTING

<160> NUMBER OF SEQ ID NOS: 16

<210> SEQ ID NO 1
<211> LENGTH: 23
<212> TYPE: DNA
<213> ORGANISM: Artificial Sequence
<220> FEATURE:
<223> OTHER INFORMATION: PPAR gamma forward

<400> SEQUENCE: 1
aggccgagaa ggagaagctg ttg                                              23

<210> SEQ ID NO 2
<211> LENGTH: 22
<212> TYPE: DNA
<213> ORGANISM: Artificial Sequence
<220> FEATURE:
<223> OTHER INFORMATION: PPAR gamma reverse

<400> SEQUENCE: 2
tggccacctc tttgctctgc tc                                               22

<210> SEQ ID NO 3
<211> LENGTH: 20
<212> TYPE: DNA
<213> ORGANISM: Artificial Sequence
<220> FEATURE:
<223> OTHER INFORMATION: C/EBP alpha forward

<400> SEQUENCE: 3
gcaaagccaa gaagtcggtg                                                  20

<210> SEQ ID NO 4
<211> LENGTH: 20
<212> TYPE: DNA
<213> ORGANISM: Artificial Sequence
<220> FEATURE:
<223> OTHER INFORMATION: C/EBP alpha reverse

<400> SEQUENCE: 4
aggcggtcat tgtcactggt                                                  20

<210> SEQ ID NO 5
<211> LENGTH: 20
<212> TYPE: DNA
<213> ORGANISM: Artificial Sequence
<220> FEATURE:
<223> OTHER INFORMATION: FABP4 forward

<400> SEQUENCE: 5
catcagcgta aatggggatt                                                  20

<210> SEQ ID NO 6
<211> LENGTH: 20
<212> TYPE: DNA
<213> ORGANISM: Artificial Sequence
<220> FEATURE:
```

<223> OTHER INFORMATION: FABP4 reverse

<400> SEQUENCE: 6
tcgactttcc atcccacttc                                                    20

<210> SEQ ID NO 7
<211> LENGTH: 21
<212> TYPE: DNA
<213> ORGANISM: Artificial Sequence
<220> FEATURE:
<223> OTHER INFORMATION: GLUT4 forward

<400> SEQUENCE: 7
ctccttctat ttgccgtcct c                                                  21

<210> SEQ ID NO 8
<211> LENGTH: 21
<212> TYPE: DNA
<213> ORGANISM: Artificial Sequence
<220> FEATURE:
<223> OTHER INFORMATION: GLUT4 reverse

<400> SEQUENCE: 8
ctgttttgcc cctcagtcat t                                                  21

<210> SEQ ID NO 9
<211> LENGTH: 21
<212> TYPE: DNA
<213> ORGANISM: Artificial Sequence
<220> FEATURE:
<223> OTHER INFORMATION: FASN forward

<400> SEQUENCE: 9
ggctctatgg attacccaag c                                                  21

<210> SEQ ID NO 10
<211> LENGTH: 19
<212> TYPE: DNA
<213> ORGANISM: Artificial Sequence
<220> FEATURE:
<223> OTHER INFORMATION: FASN reverse

<400> SEQUENCE: 10
ccagtgttcg ttcctcgga                                                     19

<210> SEQ ID NO 11
<211> LENGTH: 20
<212> TYPE: DNA
<213> ORGANISM: Artificial Sequence
<220> FEATURE:
<223> OTHER INFORMATION: beta-actin forward

<400> SEQUENCE: 11
catgtacgtt gctatccagg                                                    20

<210> SEQ ID NO 12
<211> LENGTH: 20
<212> TYPE: DNA
<213> ORGANISM: Artificial Sequence
<220> FEATURE:
<223> OTHER INFORMATION: beta-actin reverse

<400> SEQUENCE: 12
ctccttaatg tcacgcacga                                                    20

```
<210> SEQ ID NO 13
<211> LENGTH: 23
<212> TYPE: DNA
<213> ORGANISM: Artificial Sequence
<220> FEATURE:
<223> OTHER INFORMATION: C/EBP-alpha mRNA forward

<400> SEQUENCE: 13
tggacaagaa cagcaacgag tac                                              23

<210> SEQ ID NO 14
<211> LENGTH: 22
<212> TYPE: DNA
<213> ORGANISM: Artificial Sequence
<220> FEATURE:
<223> OTHER INFORMATION: C/EBP-alpha mRNA reverse

<400> SEQUENCE: 14
cggtcattgt cactggtcaa ct                                               22

<210> SEQ ID NO 15
<211> LENGTH: 26
<212> TYPE: DNA
<213> ORGANISM: Artificial Sequence
<220> FEATURE:
<223> OTHER INFORMATION: GAPDH probe

<400> SEQUENCE: 15
tgcatcctgc accaccaact gcttag                                           26

<210> SEQ ID NO 16
<211> LENGTH: 26
<212> TYPE: DNA
<213> ORGANISM: Artificial Sequence
<220> FEATURE:
<223> OTHER INFORMATION: PPAR-gamma probe

<400> SEQUENCE: 16
tcggaatcag ctctgtggac ctctcc                                           26
```